US011806186B2

United States Patent
(12) United States Patent
Stroman

(10) Patent No.: US 11,806,186 B2
(45) Date of Patent: Nov. 7, 2023

(54) SLEEP MANAGEMENT DEVICE AND METHODS FOR OPERATION

(71) Applicant: Intel Corporation, Santa Clara, CA (US)

(72) Inventor: John F. Stroman, San Jose, CA (US)

(73) Assignee: Intel Corporation, Santa Clara, CA (US)

( * ) Notice: Subject to any disclaimer, the term of this patent is extended or adjusted under 35 U.S.C. 154(b) by 730 days.

(21) Appl. No.: 16/806,213

(22) Filed: Mar. 2, 2020

(65) Prior Publication Data

US 2020/0268341 A1 Aug. 27, 2020

Related U.S. Application Data

(63) Continuation of application No. 15/088,946, filed on Apr. 1, 2016, now Pat. No. 10,582,908.

(51) Int. Cl.

*A61B 7/04* (2006.01)
*A61B 5/11* (2006.01)

(Continued)

(52) U.S. Cl.

CPC ................ *A61B 7/04* (2013.01); *A61B 5/002* (2013.01); *A61B 5/02444* (2013.01); *A61B 5/08* (2013.01);

(Continued)

(58) Field of Classification Search

CPC ......... A61B 7/04; A61B 5/02444; A61B 5/08; A61B 5/4812; A61B 5/742; A61B 5/11;

(Continued)

(56) References Cited

U.S. PATENT DOCUMENTS

| | | | |
|---|---|---|---|
| 7,492,672 | B2 | 2/2009 | Cuisinier |
| 7,967,739 | B2 | 6/2011 | Auphan |

(Continued)

FOREIGN PATENT DOCUMENTS

| | | |
|---|---|---|
| WO | 2017172132 | 10/2017 |

OTHER PUBLICATIONS

"Home", Neuroon, [Online]. Retrieved from the Internet: URL: https: neuroon.com , (Accessed: Oct. 11, 2016), 7 pgs.

(Continued)

*Primary Examiner* — Christine H Matthews
*Assistant Examiner* — Joshua Daryl D Lannu
(74) *Attorney, Agent, or Firm* — Schwegman Lundberg & Woessner, P.A.

(57) ABSTRACT

Various examples are directed to sleep management devices and methods of operating the same. A sleep management device may comprise a display. The sleep management device may be programmed to detect a first wake event and select a first wake routine associated with the first wake event. The sleep management device may execute the first wake routine at least in part by modulating an output of the display for a first duration. The sleep management device may also detect a second wake event different than the first wake event and second wake routine associated with the second wake event. The sleep management device may execute the second wake routine at least in part by modulating the output of the display for a second duration longer than the first duration.

20 Claims, 9 Drawing Sheets

(51) Int. Cl.
*A61B 5/024* (2006.01)
*A61B 5/08* (2006.01)
*A61B 5/00* (2006.01)
*A61M 21/00* (2006.01)

(52) U.S. Cl.
CPC .............. *A61B 5/11* (2013.01); *A61B 5/4812* (2013.01); *A61B 5/7282* (2013.01); *A61B 5/742* (2013.01); *A61M 21/00* (2013.01); *A61B 2560/0242* (2013.01); *A61M 2021/0027* (2013.01); *A61M 2021/0044* (2013.01)

(58) Field of Classification Search
CPC ............ A61B 5/002; A61B 2560/0242; A61B 5/7282; A61M 2021/0027; A61M 21/00; A61M 2021/0044
See application file for complete search history.

(56) References Cited

U.S. PATENT DOCUMENTS 8,493,220 B2 7/2013 Virtanen et al.
8,932,199 B2 1/2015 Berka et al.
10,582,908 B2 3/2020 Stroman
2006/0293608 A1 12/2006 Rothman et al.
2007/0249952 A1* 10/2007 Rubin .................. A61M 21/00 600/544
2007/0273611 A1* 11/2007 Torch ...................... G06F 3/013 345/8
2009/0207028 A1 8/2009 Kubey et al.
2010/0102971 A1* 4/2010 Virtanen ................. A61B 5/11 381/122
2013/0060306 A1 3/2013 Colbausch
2013/0278631 A1* 10/2013 Border .................. G06Q 30/02 345/633
2014/0303428 A1* 10/2014 Berka ................. A61B 5/6803 600/27
2016/0015315 A1 1/2016 Auphan et al.
2016/0151603 A1* 6/2016 Shouldice .............. G10L 15/26 600/26
2017/0094046 A1* 3/2017 Raymann .............. H04L 67/535
2017/0189639 A1* 7/2017 Mastrianni ............ A61B 5/378
2017/0281119 A1 10/2017 Stroman

OTHER PUBLICATIONS

"International Application Serial No. PCT US2017 019103, International Search Report dated Jun. 2, 2017", 3 pgs.
"International Application Serial No. PCT US2017 019103, Written Opinion dated Jun. 2, 2017", 8 pgs.
"International Application Serial No. PCT US2017 019103, International Preliminary Report on Patentability dated Oct. 11, 2018", 10 pgs.
"U.S. Appl. No. 15/088,946, Non Final Office Action dated May 31, 2019", 14 pgs.
"U.S. Appl. No. 15/088,946, Response filed Sep. 30, 2019 to Non-Final Office Action dated May 31, 2019", 12 pgs.
"U.S. Appl. No. 15/088,946, Notice of Allowance dated Oct. 28, 2019", 9 pgs.
Popovic, Djordje, "Wearable Modular Device for Facilitation of Napping and Optimization of Post-nap Performance", Proceedings of the 5th International Conference on Foundations of Augmented Cognition. Neuroergonomics and Operational Neuroscience: Held as Part of HCI International, (2009), 289-298.
U.S. Appl. No. 15/088,946, now U.S. Pat. No. 10,582,908, filed Apr. 1, 2016, Sleep Management Device and Methods for Operation.

* cited by examiner

SLEEP MANAGEMENT DEVICE AND METHODS FOR OPERATION

PRIORITY

This application is a continuation of U.S. patent application Ser. No. 15/088,946, filed Apr. 1, 2016, which is incorporated by reference herein in its entirety.

TECHNICAL FIELD

Examples described herein generally relate to sleep management devices and methods of operating sleep management devices.

BACKGROUND

Sleep management devices are used to improve the quality of sleep for users.

BRIEF DESCRIPTION OF THE DRAWINGS

In the drawings, which are not necessarily drawn to scale, like numerals may describe similar components in different views. Like numerals having different letter suffixes may represent different instances of similar components. Some examples are illustrated by way of example, and not limitation, in the figures of the accompanying drawings in which.

DETAILED DESCRIPTION

Figure 1:
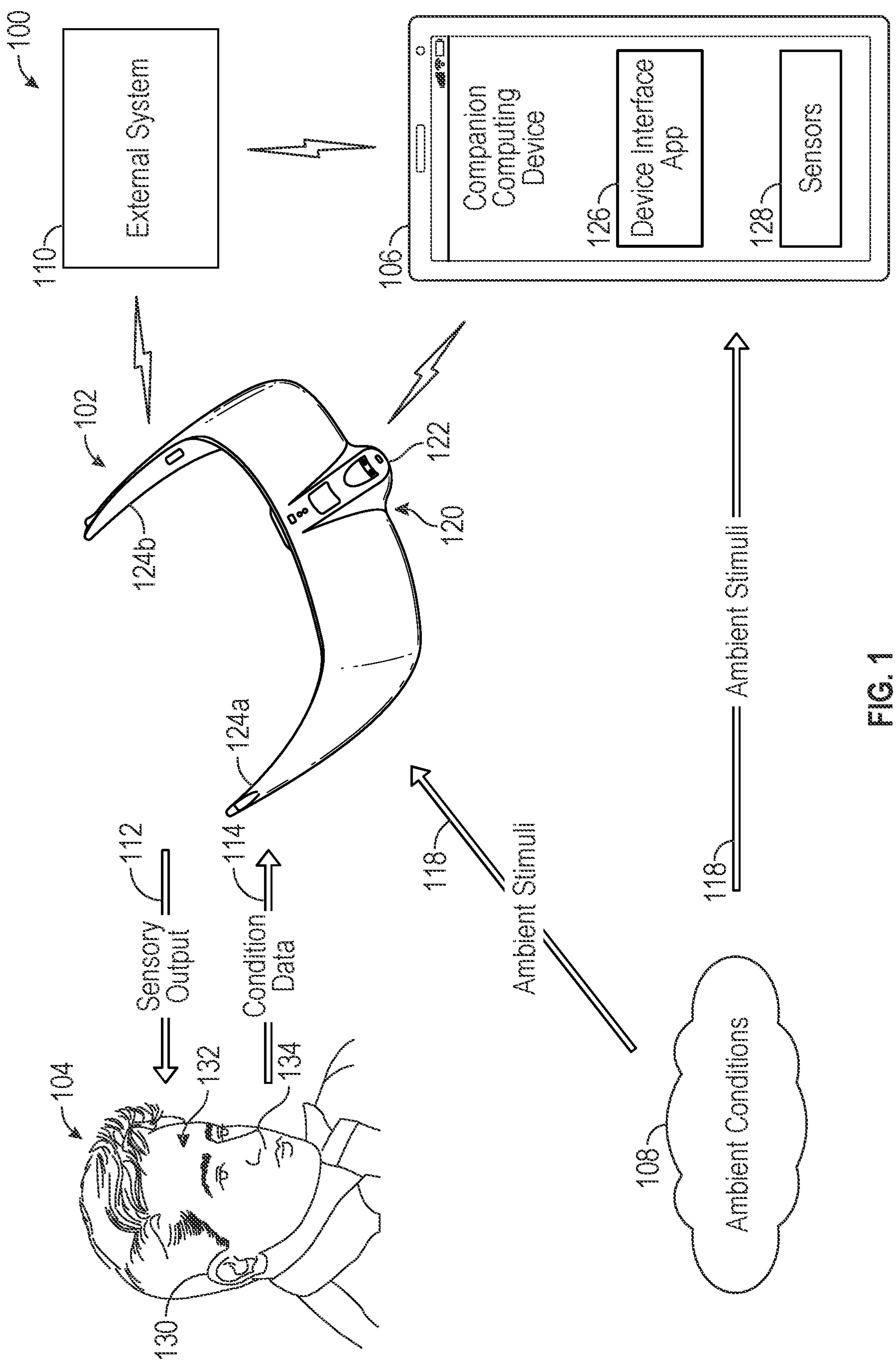
FIG. 1 is a diagram showing one example of an environment for using a sleep management device.

In the following description, for purposes of explanation, numerous specific details are set forth in order to provide a thorough understanding of some examples. It will be evident, however, to one skilled in the art that the present disclosure may be practiced without these specific details.

Various examples described herein are directed to sleep management devices and/or methods of operating sleep management devices. An example sleep management device comprises one or more displays that are visible to a user to produce visual outputs. Some examples also comprise one or more speakers or other audio output devices that are audible to the user to generate sound outputs, haptic feedback devices felt by the user, etc. A control circuit may include a processor programmed to modulate the display(s) and/or the speaker(s) to generate the visual and/or sound outputs.

The sleep management device may provide the visual and/or sound outputs to a user to regulate the user's sleep. In some examples, the sleep management device can execute a sleep inducement routine. During the sleep inducement routine, the processor circuit may modulate the display and/or the speaker to generate visual and/or sound outputs that induce sleep in the user. In some examples, the sleep management device can execute a wake routine. During the wake routine, the processor circuit may modulate the display and/or the speaker to generate visual and/or sound outputs that rouse the user from sleep.

In some examples, the sleep management device also includes one or more sensors positioned to sense conditions of the user. For example, the sleep management device may comprise a microphone sensor positioned adjacent or otherwise near an artery of the user when the sleep management device is worn. The microphone sensor may capture sounds of the user's heartbeat. In some examples, the sleep management device may comprise a microphone sensor positioned adjacent or otherwise near the user's nose or other breathing passage. The microphone sensor may capture sounds of the user's breathing. Also, in some examples, the sleep management device may comprise a thermistor or other suitable temperature sensor positioned to capture a body temperature of the user.

The sleep management device described herein may be utilized in a number of different situations or use cases. In one example, the sleep management device may be used by crew members on ships at sea. Many ships operate on shift schedules while at sea. A crew member user may utilize a sleep and/or wake routine of the sleep management device to obtain quality sleep while still waking up on time for the crew member's next shift. In another example, the sleep management device may be used by traveler users to fall asleep and wake up at appropriate times and to preemptively address jet lag.

In another example use case, the sleep management device may use sensors to detect an undesirable sleep condition. For example, the user may be sleeping with his or her head at a harmful angle, may be sleeping on his or her stomach, etc. When the sleep management device detects an undesirable sleep condition, it may be programmed to modulate the display and/or the speaker to affect the user's sleep, for example, by awakening the user and/or by providing visible and/or sound output to modify the user's sleep condition. Also, for example, the sleep management device may be used to awaken a user upon the occurrence of a wake event. The wake event may be an external sound (e.g., a fire alarm), an event added to the user's calendar, an event detected by a companion device or external system, etc.

FIG. 1 is a diagram showing one example of an environment 100 for using a sleep management device 102. The environment 100 comprises an example sleep management device 102, an example user 104, an example companion computing device 106 and an example external system 110.

The sleep management device 102 may comprise a front frame portion 120, temple arms 124*a*, 124*b* and a bridge portion 122. In some examples, the sleep management device 102 may be wearable by the user 104. The temple arms 124*a*, 124*b* may rest over the ears of the user 104. For example, the temple arm 124*a* may rest on the user's ears 130. The front frame portion 120 may be positioned over the user's eyes 132 and a portion (e.g., the bridge) of the user's nose 134. The front frame portion may have a distal side that is directed away from the user 104 when the sleep management device 102 is worn and a proximal side that is directed towards the user 104 when the sleep management device 102 is worn.

The front frame portion 120 may include the one or more displays. Displays may be placed and/or visible from the proximal side of the front frame portion 120. For example, the display or displays may be directed towards the user's eyes 132 when the user 104 wears the sleep management device 102. The one or more speakers may be positioned on or in the temple arms 124*a*, 124*b* and/or connected thereto. The bridge portion 122 may include a control circuit for the sleep management device 102 including various sensors and electronics such as, the processor circuit, a battery, input/output (I/O) ports, etc.

The sleep management device 102 may provide sensory output 112 to the user 104 and receive condition data 114 from the user. Sensory output 112 may include visual output provided by the one or more displays and/or sound output provided by the one or more speakers. In some examples, the sleep management device 102 may have additional output components for providing additional outputs to the user. Condition data 114 may include data describing the user 104 sensed by a one or more sensors of the sleep management device 102. In some examples, the condition data 114 includes temperature data describing a temperature of the user 104 sensed by a temperature sensor of the sleep management device 102. In some examples, the condition data 114 includes heart rate data sensed by a heart rate sensor of the sleep management device 102. In some examples, the condition data 114 includes breathing rate data sensed by a breathing rate sensor of the sleep management device 102. For example, breathing rate data may indicate episodes of sleep apnea in the user 104. The sleep management device may store data describing sleep apnea as condition data 114 for later analysis and/or may take actions to mitigate sleep apnea, for example, as described herein at FIG. 13. In some examples, the condition data 114 includes orientation data describing orientation of the user 104 sensed by one or more gyroscopic sensors and/or accelerometers of the sleep management device 102. In some examples, the condition data 114 includes motion data describing a motion of the user sensed by one or more gyroscopic sensors and/or accelerometers of the sleep management device 102. Example configurations of the sleep management device 102, including arrangements of the one or more displays, speakers, sensors, etc., are provided herein with FIGS. 2-8.

In some examples, the sleep management device 102 may be in communication with a companion computing device 106. The companion computing device 106 may be any suitable computing device such as, for example, a tablet computer, a mobile phone, a laptop or desktop computer, etc. In some examples, the companion computing device 106 may execute a device interface application 126. The device interface application 126 may provide to the user 104 a graphical user interface for configuring the sleep management device 102. In some examples, the device interface application 126 may also receive sensor data from one or more sensors 128 of the companion computing device 106. The sensors 128 may include, for example, a Global Positioning System (GPS) sensor, one or more accelerometers, one or more gyroscopic sensors, one or more microphone sensors, one or more temperature sensors, one or more cameras, etc. In some examples, the device interface application 106 may provide instructions to the sleep management device 102 based at least in part on stimuli sensed by the one or more sensors 128.

The companion computing device 106 may communicate with the sleep management device 102 in any suitable manner. For example the companion computing device 106 and sleep management device 102 may communicate utilizing any suitable wired, wireless, or mixed network including a packet-switched network, such as the Internet, a mobile telephone network, etc. In some examples, the sleep management device 102 and the companion computing device 106 may communicate via a short range wireless communication medium such as, for example, BLUETOOTH, BLUETOOTH LE, Near Field Communication (NFC) link, an infrared link, etc. Also, in some examples, the sleep management device 102 and companion computing device 106 may communicate via a wired link, such as a Universal Serial Bus (USB) link.

In some examples, the sleep management device 102 and/or the companion computing device 106 communicates with an external system 110. The external system 110 may be any suitable type of computing device including, for example, a mobile computing device, a server, a cloud-implemented system, etc. Example external systems 110 may include a security system for a home or other premises, a smoke detector or other fire detection system, a spacecraft control server monitoring/managing the sleep of astronauts, etc. In some examples, the external system 110 may be and/or include a hotel server system implementing wake-up calls for guests through the sleep management device 102, a ship or aircraft server system managing the sleep of passengers or crew members, etc.

The external system 110 may, in some example, provide alerts and/or other data for controlling the sleep management device 102 to the sleep management device 102 and/or to the companion computing device 106. The external system 110 may communicate with the companion computing device 106 and/or the sleep management system 102 in any suitable manner including, for example, a wired, wireless, or mixed packet-switched network, a mobile phone network, a short range communications medium, etc. The external system 110 may communicate with the sleep management device 102 directly. In some examples, the external system 110 may communicate with the sleep management device 102 indirectly through the companion computing device 106 (e.g., the device interface application 126 thereof).

The environment 100 also shows ambient conditions 108. Ambient conditions may include any sensory conditions at or near the sleep management device 102 and/or the companion computing device. Example ambient conditions 108 may include, temperature, noises, light levels, the presence or absence of a television or other moving screen, etc. Ambient conditions 108 may provide ambient stimuli 118 to the sleep management device 102 and/or to the companion computing device 106. For example, when the ambient conditions 108 include a light level, the light may provide ambient stimuli 118 to a sensor of the sleep management device 102 and/or the companion computing device 106. Also, for example, when the ambient conditions 108 include a noise, sound waves constituting the noise may provide an ambient stimuli 118 to a sensor of the sleep management device 102 and/or the companion computing device 106. In some examples, the external system 110 may also sense ambient conditions, for example, at or around the external system 110.

Figure 2:
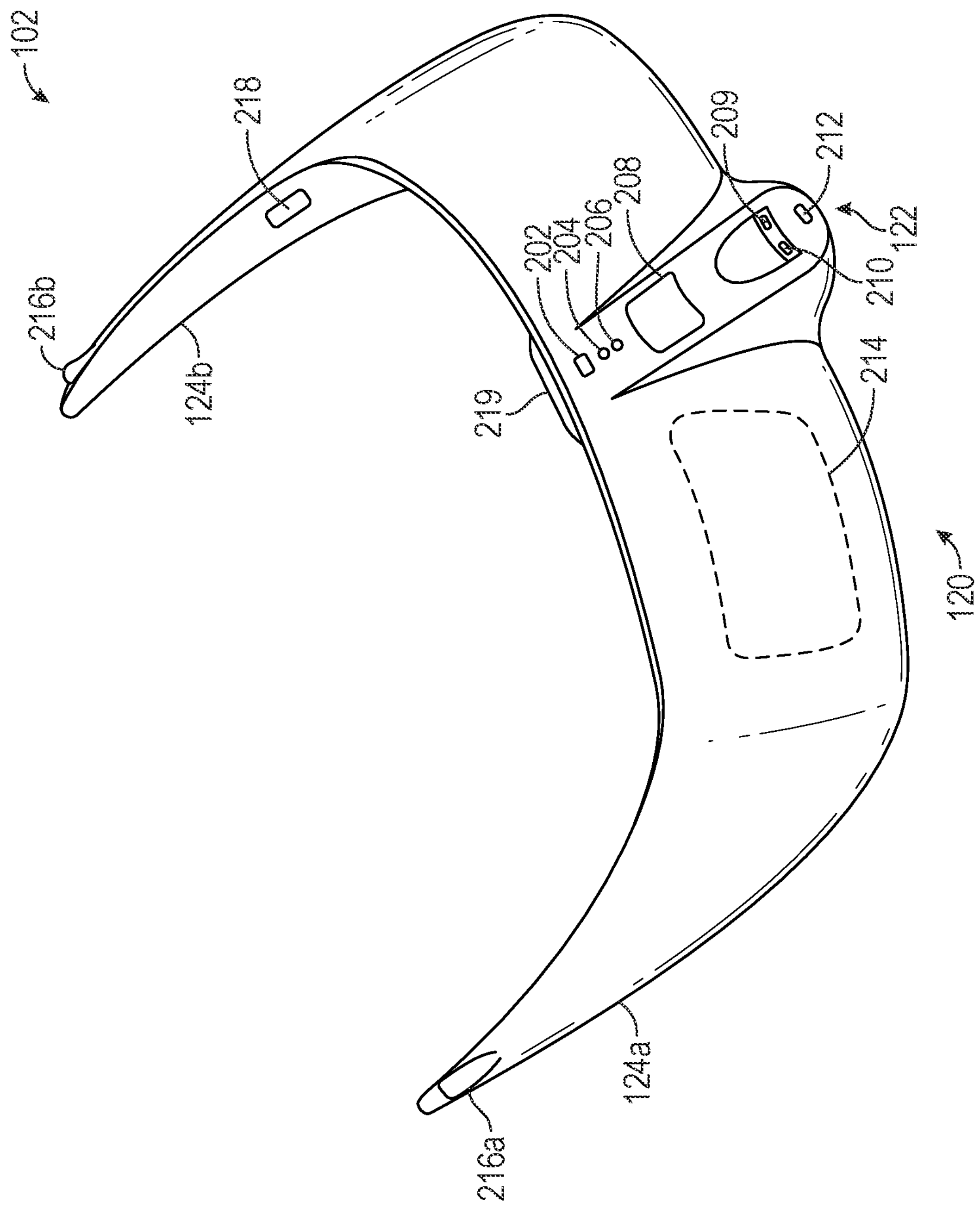
FIG. 2 is a diagram showing one example configuration of a sleep management device.

FIG. 2 is a diagram showing one example configuration of the sleep management device 102 of FIG. 1. In the example of the sleep management device 102 shown in FIG. 1, various electronics for controlling the sleep management device 102 are positioned at the bridge portion 122. For example, the bridge portion 122 includes a power switch 202. The power switch 202 may be actuated (e.g., by the user 104) to turn the sleep management device 102 on or off. An on/off indicator light 204 may be illuminated to indicate the on or off status of the sleep management device 102. In some examples, the light 204 is a Light Emitting Diode (LED). In some examples, the light 204 may be illuminated when the sleep management device 102 is on and not illuminated when the sleep management device 102 is off. In some examples, a color of the light 204 may also indicate a status of the sleep management device 102. For example, when the sleep management device 102 determines that the user 104 is asleep or otherwise not to be disturbed, the light 204 may be illuminated at a first color (e.g., red). When the sleep management device 102 determines that the user 104 is awake and available to be disturbed, the light be illuminated at a second color different than the first color (e.g., green). This may indicate to people around the user 104 whether the user 104 may is to be disturbed.

In some examples, the bridge portion 122 may also include a charge light 206, which may also be an LED. The charge light 206 may be illuminated when a battery of the sleep management device 102 (FIG. 3) is charging. The battery, in some examples, may be removable. For example, FIG. 2 shows a battery panel 208 on the bridge portion 122. The battery panel 208 may be removable to access and/or remove the battery of the sleep management device 102. In some examples, the bridge portion 122 may further include a microphone sensor 212. The microphone sensor 212 may be positioned to sense sound from the user's breathing, thereby allowing the sleep management device to measure a breathing rate and/or related metrics for the user 104. For example, the microphone sensor 212 may be placed near to the user's nasal passages. When air enters the user's nasal passages during inhalation or exits the user's nasal passages during exhalation, it may create a sound. The control circuit may receive a signal from the microphone sensor 212 that reflects the sound of inhalation and exhalation. From the signal, the control circuit may determine a breathing rate for the user 104. In some examples, the microphone sensor 212 may also or alternatively be positioned to sense external or ambient sounds, such as generated by alarms, approaching people, etc. The microphone sensor 212 may be used to sense user breathing, external stimuli, or both.

The bridge portion 122 also comprises a charging interface or plug 208 and/or a wired data interface or plug 210. The charging interface 209 may be configured to receive a wired connection providing an electric current for charging the battery of the sleep management device 102. The data interface 210 may be configured to receive a wired connection providing data to the sleep management device 102 according to any suitable wired protocol, such as a serial or parallel protocol. In some examples, the charging interface 209 and the data interface 210 may be combined into a common charging and data interface, such as a Universal Serial Bus (USB). Also, in some examples, the charging interface 209 and/or the data interface 210 may be omitted. For example, the sleep management device 102 may communicate wirelessly. Also, in some examples, the sleep management device 102 may be charged wirelessly, such as, for example, utilizing an inductive charging mechanism.

In some examples, a skin contact pad 219 may be positioned on the front frame portion 120, e.g., at a back or proximal side of the front frame portion 120 such that the skin contact pad 219 is in physical contact with the skin of the user 104 when the user wears the sleep management device 102. The skin contact pad 219 may include various sensors for sensing conditions of the user including, for example, a temperature sensor for sensing a skin temperature of the user, a galvanic sensor for sensing moisture content on the user's skin, etc. Also, in some examples, the skin contact pad 219 may include components that move with the user's face. Motion sensors such as accelerometers and/or gyroscopic sensors, may be in contact with the skin contact pad 219 to move with the user's face, thereby providing condition data to the sleep management device 102. Additional details of the configuration of sensors at the skin contact pad 219 are shown in FIG. 3.

FIG. 2 also illustrates one example position for a heart rate sensor 218. The heart rate sensor 218 may be any suitable type of sensor, such as, for example, a microphone. In some examples, when the user 104 wears the sleep management device 102, the heart rate sensor 218 may be positioned at or near the superficial temporal artery or other suitable artery or vein in the user's temple. The artery, vein or blood therein may make a noise as blood pumps through it. The heart rate sensor 218 may capture the noise. The control circuit may receive a signal from the heart rate sensor 218 and derive the user's heartbeat. For example, each beat of the user's heart may be represented by an increase in the intensity of the sound signal received by the sensor 218. From the user's heartbeat, the control circuit may derive the users' heart rate, as described herein. Although the heart rate sensor 218 is illustrated as a microphone sensor to be positioned at the user's temple, in various other examples, the heart rate sensor 218 may be of other suitable types and/or placed at other suitable positions.

FIG. 2 also shows an outline 214 showing the position of a display panel of the sleep management device. Additional details of the display panels are shown in FIG. 3. In addition, FIG. 2 shows speaker sockets 216*a*, 216*b*. The speaker sockets 216*a*, 216*b* may receive plugs from one or more external speakers (not shown in FIG. 2) that may be used by the sleep management device 102 to generate sound outputs. Additional details of speakers and temple arm 124*a*, 124*b* configurations are shown in FIGS. 4-7.

Figure 3:
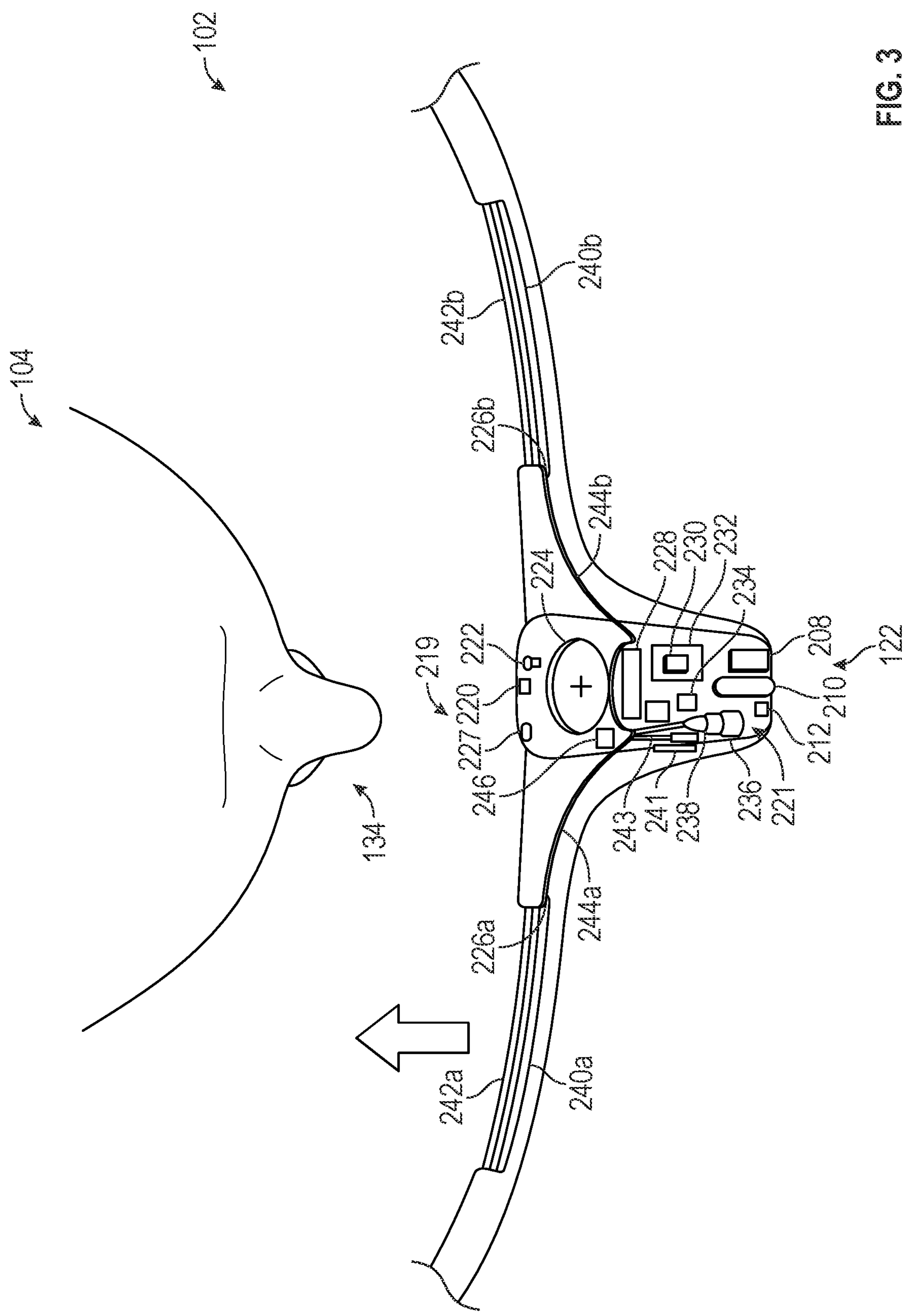
FIG. 3 is a diagram showing a cross-sectional view of the example sleep management device in conjunction with a user.

FIG. 3 is a diagram showing a cross-sectional view of the example sleep management device 102 in conjunction with the user 104. FIG. 3 shows some of the components of the sleep management device 102 visible in FIG. 2 as well as additional internal components. For example, FIG. 3 shows the charging interface 209, data interface 210, and microphone sensor 212 described above.

A control circuit 221 for the sleep management device 102 may be positioned at the bridge portion 122 and may include various components described herein. The charging interface 209, data interface 210 and microphone sensor 212 may be mounted at the control circuit 221. Additionally, the control circuit 221 may include a processor 230. The processor 230 may comprise any suitable microprocessor, digital signal processor (DSP) or other suitable processing device.

In some examples, a heat sink 232 may be positioned near the processor and, in some examples, may be in physical contact with the processor, to conduct away heat generated by the processor 230. Any suitable heat sink 233 may be used. Although one heat sink 232 is shown, additional heat sinks may be used for the processor 230 and/or other components of the processor circuit. A memory 228 may include any suitable type of volatile or non-volatile memory or any other type of data storage. In some examples, memory 228 may include electrically erasable and reprogrammable (EEPROM) flash memory.

The control circuit 221 may include an antenna 243, which may be utilized for wireless communications with the companion computing device 106, the external system 110 and/or another device. The control circuit 221 may also comprise an audio amplifier 241 that may be electrically coupled to one or more speakers (not shown in FIG. 3) to drive the speakers, for example, in response to instructions from the processor 230. The audio amplifier 241 and speakers may be part of an audio system of the sleep management device 102 for generating sound output.

Some examples may include an input/output (I/O) hub 234 to interface with some or all of the I/O components of the sleep management device 102. For example, the I/O hub 234 may comprise suitable digital-to-analog (DAC) components. The I/O hub 234 may be any suitable device for handling input and output to the processor 230. For example, the I/O hub 234 may receive input signals from various sensors 212, 218, 220, 222, etc. The I/O hub 234 may also receive input signals via communications devices such as, for example, the data interface 210, antenna 243, etc. The I/O hub 234 may also provide outputs to the display system, described below, for example by driving the illumination source 236 in response to instructions from the processor 230. The I/O hub 234, in some examples, may also drive the speaker(s) (not shown in FIG. 3), for example, via the audio amplifier 241. The control circuit 221, in some examples, may also include the battery 224, which may be accessible behind the battery panel 208, as described above. A voltage controller 246 may include any suitable switches or other circuit components for regulating the voltage provided by the battery 224. Various components of the control circuit 221 are shown. It will be appreciated that a control circuit for a sleep management device 102 may include more or fewer components than are shown.

In some examples, the control circuit 221 may also comprise and/or be in communication with additional sensors 220, 222. Temperature sensor 220, for example, may be positioned at the skin contact pad 219 to sense a temperature of the user's skin. Motion sensor 222 may be positioned to move as the user's head moves and may provide a signal indicating an orientation and/or motion of the user's head. In some examples, a haptic output device 227 may be positioned at the skin contact pad 210, as shown, or at any other suitable location (e.g., on temple arms 124*a* or 124*b* and positioned to affect the user's temples).

FIG. 3 also shows an example display system of the sleep management device 102. The display system may include an illumination source 236, an optical splitter 238, light pipes 244*a*, 244*b*, display panels 240*a*, 240*b*, and windows 242*a*, 242*b*. The illumination source 236 may be positioned at the bridge portion 122 and, in some examples, may be in electrical communication with various components of the control circuit such as, for example, the processor 230, the I/O hub 234, etc. In some examples, the illumination source 236 may be positioned on a common circuit board with some or all of the components of the control circuit 221. In some examples, the illumination source 236 may be a multi-color source such as, for example, a Red/Green/Blue (RGB) LED. An RGB LED or other similar illumination source may be used to generate multiple colors at the display panels 240*a*, 240*b*.

The illumination source 236 may be optically coupled to the optical splitter 238, for example, with an optical glue or other suitable component or material. The optical splitter 238 may be of any suitable type such as, for example, a Fused Biconical Taper (FBT) splitter, a Planar Lightwave Circuit (PLC) splitter, mirror, bulk splitter, etc. The optical splitter 238 may have two outputs and may split light generated by the illumination source 236 into two components, one provided at each of the outputs. The optical splitter 238 may have a 50/50 split ratio, although optical couplers with any suitable split ratio may be used. In some examples, a split ratio of the optical splitter 238 may be controlled by the processor circuit of the sleep management device 102.

The outputs of the optical splitter 238 may be optically coupled to respective light pipes 244*a*, 244*b*, which optically connect the optical splitter 238 to the display panels 240*a*, 240*b*. Light pipes 244*a*, 244*b* may be made from any suitable material or materials that transmits light at the desired wavelength or wavelength range. The light pipes 244*a*, 244*b* may be optically coupled to respective display panels 240*a*, 240*b*. For example, light pipe 244*a* may be optically coupled to display panel 240*a* and light pipe 244*b* may be optically coupled to display panel 240*b*. The light pipes 244*a*, 244*b* may be optically coupled to the respective display panels 240*a*, 240*b* using any suitable material or technique including, for example, an optical glue.

The display panels 240*a*, 240*b* may distribute light received from the light pipes 244*a*, 244*b*, from the illumination source 236, for example, evenly or nearly evenly. The display panels 240*a*, 240*b* may use any suitable light diffusion material or technique. In some examples, the sleep management device 102 may comprise windows 242*a*, 242*b* positioned outside of the respective display panels 240*a*, 240*b*. The windows 242*a*, 242*b* may be made from plastic or another durable material. Windows 242*a*, 242*b* may protect the display panels 240*a*, 240*b* from damage, including damage due to sweat, make-up, etc., from the user 104. Windows 242*a*, 242*b*, in some examples, may also protect the user 104 by preventing components of the sleep management device 102 from protruding due to wear and/or impact.

In the example display system shown in FIG. 3, the display panels 240*a*, 240*b* are passive. For example, the illumination source 236 is remote from the display panels. In some examples, this may minimize the heat generated by the illumination source that is conducted to the user 104.

Figure 4:
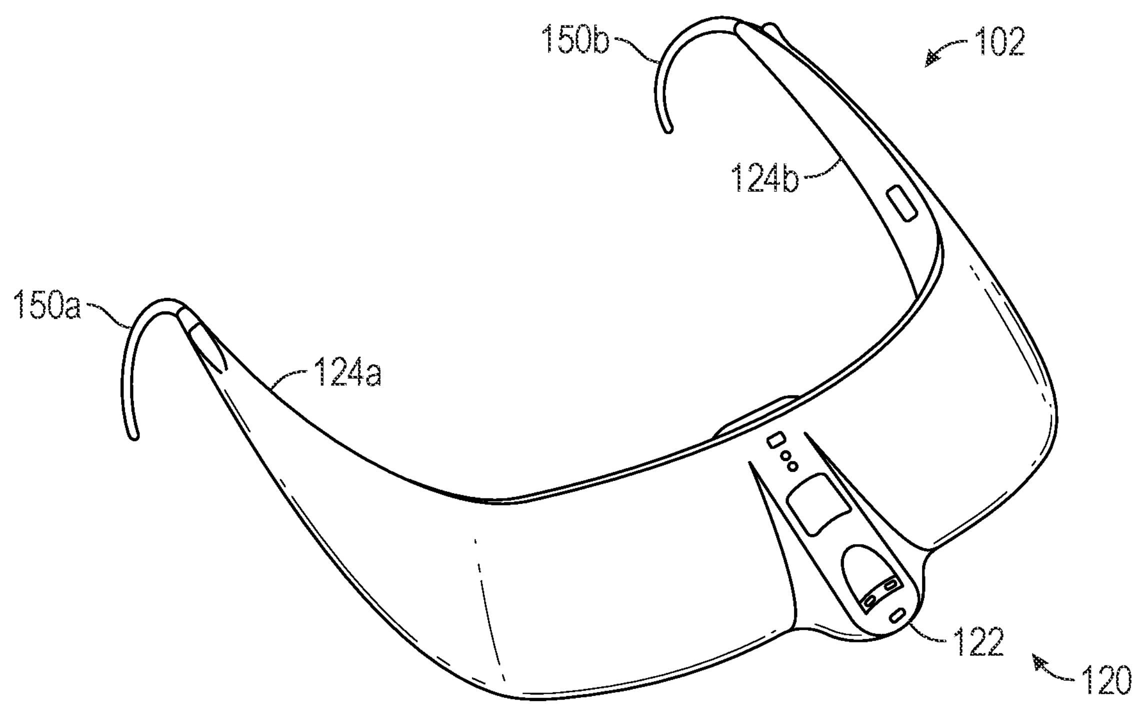
FIGS. 4-7 show example configurations of the temple arms of the sleep management device.
Figure 5:
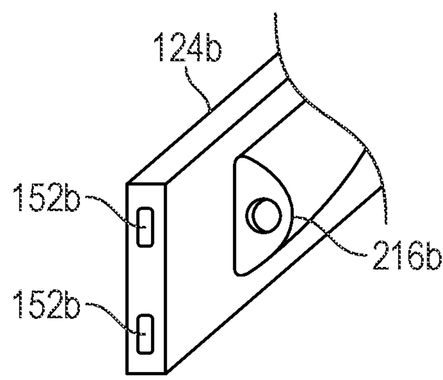
Figure 6:
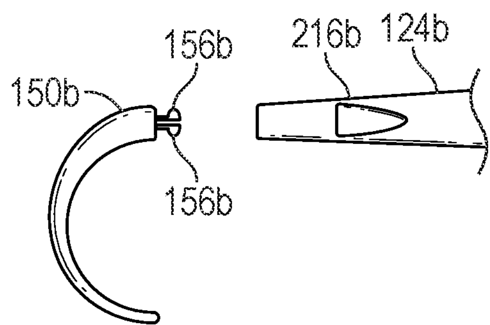

FIGS. 4-7 show example configurations of the temple arms 124*a*, 124*b* of the sleep management device 102. For example, FIG. 4 shows one example of the sleep management device 102 comprising curved ear pieces 150*a*, 150*b*. Curved ear pieces 150*a*, 150*b* may fit around the ears (e.g., 130) of the user 104 to secure the sleep management device 102 to the user 104. The curved ear pieces 150*a*, 15*b* may be integral to the temple arms 124*a*, 124*b* and/or may be removable. For example, FIG. 5 shows an end of the temple ear piece 124*b* showing a socket pattern 152*b* for receiving the curved ear piece 150*b*. FIG. 6 shows another view of one example of the temple arm 124*b* and curved ear piece 150*b*. As shown in FIG. 6, the curved ear piece 150*b* may comprise pegs 156*b* that may be received into the socket patter 152*b* of the temple arm 124*b*. Although two pegs 156*b* and a two-hole socket pattern 152*b* are shown, any suitable number of pegs may be used.

Figure 7:
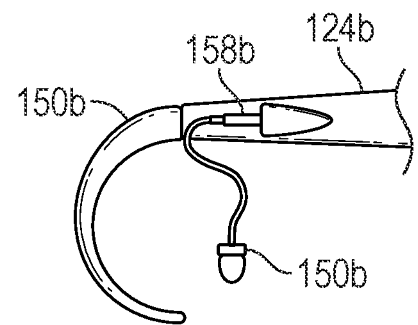

In some examples, a speaker or speakers may be incorporated into the temple arms 124*a*, 124*b* and/or the curved ear pieces 150*a*, 150*b*. In other examples, however, the sleep management device 102 may comprise one or more sockets for receiving a speaker. For example, FIG. 5 shows a socket 216*b* positioned at the temple arm 124*b*. The socket 216*b* may receive a jack 158*b* of an earbud 160*b* or other suitable speaker. In some examples, both temple arms 124*a*, 124*b* may include sockets for receiving a speaker. In other examples, a single socket may receive a single jack that operates two speakers (e.g., one for each ear). Although FIG. 7 shows an earbud-type speaker 160*b*, any suitable headphone or other speaker may be used. In some examples, a speaker may cover one or both of the ears so as to block out ambient sound. Also, in some examples, an active noise-cancellation speaker may be used.

Figure 8:
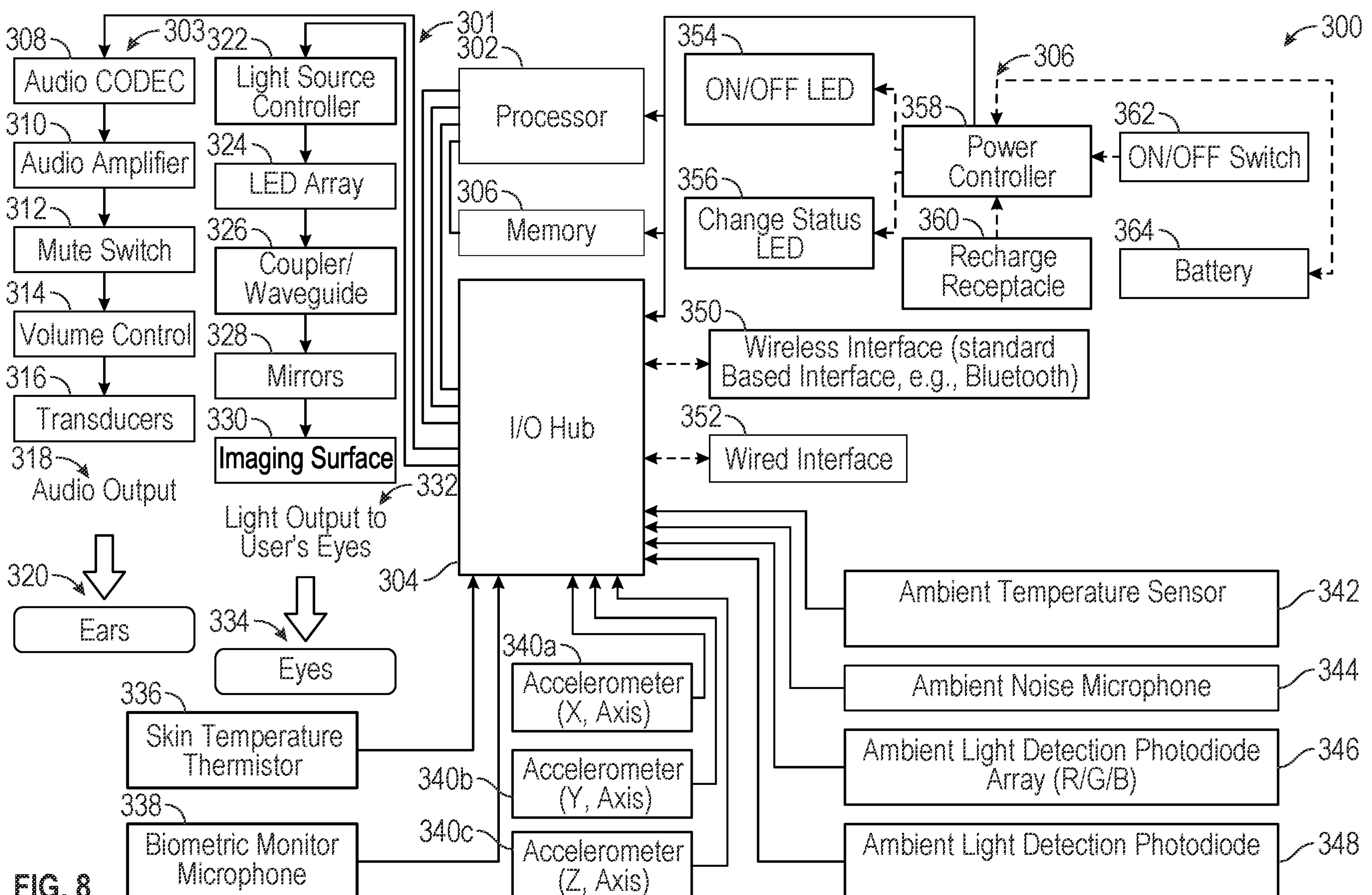
FIG. 8 is a system diagram showing one example system architecture for the sleep management device.

FIG. 8 is a system diagram showing one example system architecture 300 for the sleep management device 102. The architecture 300 may include hardware and/or software components. Items similar to some of the components of the architecture are described herein above with respect to FIGS. 2-7.

The architecture 300 may comprise a processor 302 and memory 306, for example, similar to the processor 230 and memory 228 described herein above. An I/O hub 304, similar to the I/O hub 234 described herein. The I/O hub 304 may be in communication with various systems and subsystems of the architecture to facilitate inputs and outputs. In some examples, the I/O hub 304 may be in communication with a wireless interface 350 for communicating according to short range communication medium or other wireless standard. A wired interface 352 may facilitate communications according to a wired protocol such as, for example, Universal Serial Bus (USB).

An audio system 303 for generating a sound output. The audio system 303 may comprise various components including, for example an audio CODEC 308, an audio amplifier 310, a mute switch 312, a volume control 314, and transducers or speakers 316. The audio CODEC may be a hardware or software device for decoding digital audio signals provided by the processor 302 via the I/O hub 304. The audio amplifier 310 may increase an intensity of an audio signal. For example, the audio amplifier 310 may correspond to the amplifier 241. A mute switch 312 may be a hardware or software-implemented switch selectable to disable sound output of the sleep management device. A volume control 314 may be a hardware or software implemented variable switch for setting a volume of the sound output of the sleep management device. In some examples, the mute switch 312 and/or the volume control switch may be implemented at the device interface app 126 described herein. The transducers 316 may be one or more speakers, as described herein. The result of the sound system 303 may be an audio or sound output 318 provided to the ears 320 of the user.

The architecture 300 may also comprise a display system 301. The display system 301 may comprise a light source controller 322, an LED array 324, a coupler/waveguide subsystem 326, one or more mirrors 328 and an imaging surface 330. The light source controller 322 may comprise any suitable hardware or software component for controller a light source. The LED array 324, for example, may correspond to the illumination source 236 described herein. The coupler/waveguide subsystem 326 may correspond to the optical splitter 238 and light pipes 244*a*, 244*b* described herein. Mirrors 328, in some examples, may be positioned behind the display panels 240*a*, 240*b* to minimize lost light. Imaging surfaces 330 may correspond to the display panels 240*a*, 240*b*. Light output from the imaging surfaces 330 may be provided to the eyes 334 of the user 104.

The architecture 300 also includes various sensors. A skin temperature sensor 336 may sense a temperature of the user's skin. In some examples, the skin temperature sensor 336 may correspond to the temperature sensor 220 described herein. A biometric monitor microphone sensor or microphone sensors 338 may include one or more microphone sensors positioned to sense biometric functions of the user 104, such as breathing or heart rate. For example, biometric microphone sensors may include microphone sensors 218 and 212 described herein.

The architecture 300 may also include motion sensors, including accelerometers 340*a*, 340*b*, 340*c*. Motion sensors 340*a*, 340*b*, 340*c* correspond to motion sensors 222. Accelerometers 340*a*, 340*b*, 340*c* may be positioned for example, at the skin contact pad 219. In some examples, each of the accelerometers may be oriented according to a different spatial axis so as to sense acceleration of the sleep management device 102 (and the user's head) in three dimensions. Accelerometers 340*a*, 340*b*, 340*c*, because they are in contact with the user's skin, may also sense eye movement. For example, movement of the user's eyes may cause movement in the user's skin at the bridge of the nose, which may, in turn, cause acceleration of the accelerometers 340*a*, 340*b*, 340*c*.

The architecture 300 may also include ambient sensors for detecting ambient stimuli 118. An ambient temperature sensor 342 may sense an air temperature outside of the sleep management device 102. An ambient noise microphone sensor 344 may detect noise near the sleep management device 102, generated by the user 104 or other people or things near the user 104. A visible ambient light detection photodiode 346 may detect visible light incident on the sleep management device 102. An infrared ambient detector 348 may detect infrared light incident on the sleep management device 102.

A power system 305 may include a power controller 358 and a battery 364. The power system 305 may also include an on/off switch 362, which may correspond to switch 202, an on/off LED 354, which may correspond to light 204, and a charge status LED 356, which may correspond to charge light 206. A recharge receptacle may correspond to charge interface 209.

Figure 9:
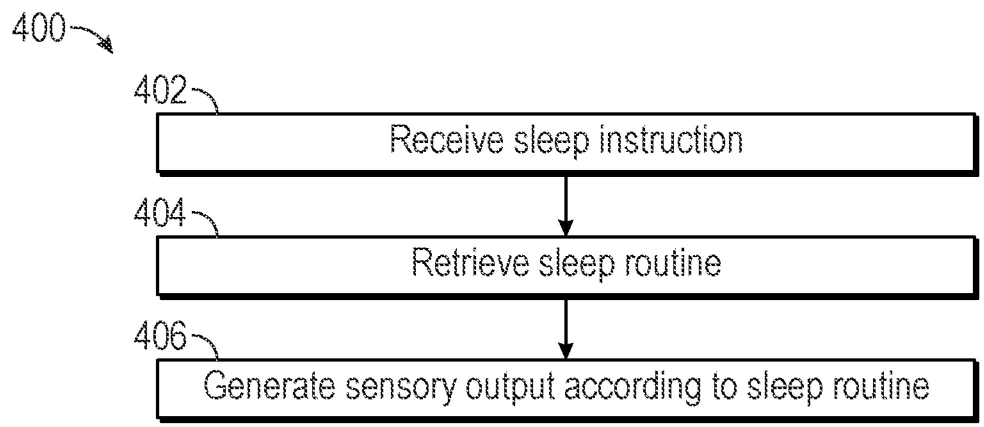
FIG. 9 is a flow chart showing one example of a process flow that may be performed by a sleep management device to induce sleep in a user.

FIG. 9 is a flow chart showing one example of a process flow 400 that may be performed by a sleep management device (e.g., a control circuit thereof), such as the device 102 described herein, to induce sleep in a user. At action 402, the sleep management device may receive a sleep instruction. The sleep instruction may comprise data instructing the sleep management device to induce sleep in the user. The sleep instruction may be received from any suitable device and/or derived in any suitable manner. In some examples, the sleep instruction may be received from a companion device. In some examples, the sleep instruction may be received from an external system. For example, if the user has indicated that he or she would like to begin sleeping at a particular time, the sleep management device or other suitable device may determine when the particular time has arrived and, at that time or before, generate the sleep instruction. In some examples, the sleep management device, or other suitable device, may receive calendar data indicating scheduled events and/or travel plans. The sleep management device or other suitable device may select an optimum time for sleep based at least in part on the user's schedule, and the time zone that the user is scheduled to be in. When the selected optimum time for sleep arrives, the sleep management device or other suitable device may generate the sleep instruction.

Optionally, the sleep management device may prompt the user to wear the device. For example, when the sleep instruction is received at action 402, the user may not be wearing the sleep management device. The sleep management device may prompt the user to wear the device in any suitable manner. For example, the sleep management device may illuminate and/or blink any suitable lights or lamps. It may also cause a speaker or speakers to emit an alarm sound or other suitable sound for alerting the user. In other examples, action 404 may be omitted. For example, the user may decide on his or her own to wear the device and may select a sleep inducement routine.

At action 404, the sleep management device may retrieve a sleep inducement routine for the user. The sleep inducement routine may comprise a set of visual and/or sound outputs to be provided to the user to induce the user to sleep. Sleep inducement routines may be open loop routines which proceed through a sequence of visible and/or sound outputs. Some sleep inducement routines may be closed loop routines, which modify the sound and/or visible outputs generated based at least in part on feedback from the user (e.g., user conditions), the ambient environment, or other factors.

Any suitable sleep inducement routine may be selected. In some examples, the sleep management device may select a sleep inducement routine based at least in part on a schedule and/or time zone of the user. For example, if the user has only a short time to sleep, an expedited sleep inducement routine may be selected to induce the user to fall asleep quickly. If the user has a longer time to sleep, a longer term sleep inducement routine may be selected. Also, in some examples, a sleep inducement routine may be selected based at least in part on ambient stimuli 118. For example, a noisy environment may prompt the sleep management device to a particular sleep inducement routine, while a quiet environment may prompt the sleep management device to a different sleep inducement routine. Similarly, the sleep management device may select different sleep management routines in ambient environments with high levels of light than in ambient environments with lower levels of light. At action 406, the sleep management device may generate sound and/or visible output to the user, for example, according to the sleep inducement routine selected at action 404.

In some examples, the user may select a sleep inducement routine. An example sleep inducement routine may be duration based. For example, the user may ask to be awakened after a predetermined time has passed (e.g., 7 hours). In some examples, the sleep inducement routine may include a contingency determined automatically and/or selected by the user. In some examples, the contingency may be a sleep condition. For example, the device may wake the user after a selected duration, but earlier if an undesirable sleep condition occurs (e.g., snoring, poor head position, etc.) In some examples, the contingency may be based on the location of the device. For example, the device may be programmed to modify the duration of the user's sleep if the user is on a plane and the flight is diverted, delayed, etc., as determined by a Global Positioning System (GPS) or other position sensor on the device. The contingency or contingencies may be determined by the user and/or may be pre-programmed. In some examples, a contingency may be set by a third party. For example, the user's supervisor may modify a sleep inducement routine to wake the user early and/or allow the user to sleep longer based on changing conditions.

Figure 10:
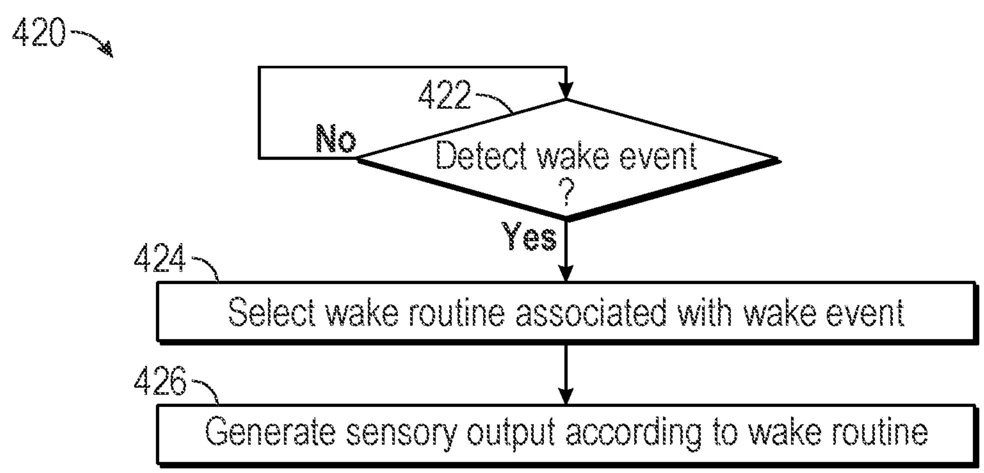
FIG. 10 is a flow chart showing one example of a process flow that may be performed by a sleep management device to wake a user.

FIG. 10 is a flow chart showing one example of a process flow 420 that may be performed by a sleep management device to wake a user. For example, the process flow 420 may be executed while the user is asleep. At action 422, the sleep management device may determine whether it has detected a wake event. If not, the sleep management device may continue to determine whether a wake event is detected at action 422, for example, periodically while the user is asleep.

Any suitable occurrence may cause the sleep management device to detect a wake event. In some examples, the sleep management device may detect a wake event at a scheduled time. For example, the user may provide the sleep management device with a scheduled wakeup time. The sleep management device may determine that a wake event has occurred when the wake time arrives. In some examples, the sleep management device may receive calendar data describing a schedule of the user (e.g., from a memory of the control circuit, from another computing device, etc.). The sleep management device may detect a wake event a threshold time period before an appointment of the user. The threshold time period may be selected to give the user time to awake, get ready for, and travel to the appointment.

In some examples, the sleep management device may detect a wake event based at least in part on ambient stimuli, such as an ambient sound. For example, a fire alarm or other sound sounding near the sleep management device may indicate a danger that the user should be awake to avoid. Accordingly, the sleep management device may detect a wake event when it detects an ambient sound. For example, the sleep management device may receive a signal representing an ambient sound from a microphone sensor. The sleep management device may detect a wake event, for example, if the ambient sound has an intensity higher than an intensity threshold, which may indicate that the ambient sound is an alarm or other potential danger. In some examples, the sleep management device (e.g., the control circuit thereof) may store digital representations of reference sounds corresponding to one or more alarms or other ambient sounds that denote a wake event. The sleep management device may detect a wake event by comparing the ambient sound (e.g., the signal representing the ambient sound) to one or more reference sound signals. If a detected ambient sound differs from a reference sound signal by less than a difference threshold, a wake event may be detected. In another example, the sleep management device may detect a wake event if the ambient temperature around the sleep management device becomes too warm (e.g., above a threshold temperature) and/or too cold (e.g., below a threshold temperature).

Also, in some examples, the sleep management device may be programmed to detect another person in close vicinity of the user. For example, if the user is sleeping in an airport or other public location, he or she may program the sleep management device to wake the user if someone approaches. The sleep management device may determine that another person has approached the user, for example, based on detecting the other person's voice, detecting noise from movement of the other person, etc. When the sleep management device detects the presence of another person, it may detect a wake event. In some examples, if the sleep management device determines that an emergency conditions has occurred, it may contact appropriate authorities.

Emergency conditions may occur when the user is or may be in danger (e.g., when an alarm sounds, when another person approaches, etc.).

In some examples, the sleep management device may detect a wake event based at least in part on a message from another computing device. In some examples, the companion computing device (such as companion computing device 106) may detect an ambient stimuli (e.g., alarm, approaching person, etc.), as described above, and send a wake message to the sleep management device. The sleep management device may detect a wake condition when it receives the wake message. In some examples, an external system may detect a wake event. For example, the external system may be or be in communication with a mobile computing device of an associate of the user (e.g., a family member, business associate, etc.) The external system may be programmed to generate a wake message when the associate travels within a predetermined geographic boundary. For example, the user may program the sleep management device to awaken the user if the user's child enters a particular neighborhood. Also, in some examples, the external system may be a burglar alarm, fire detection, or other system at the user's home or business. The external system may be programmed to generate a wake message when the burglar alarm or other system is set off or detects another condition that might require waking the user.

In some examples, the sleep management system may be programmed to detect a wake event if a predetermined sleep condition of the user is detected. One example of a user sleep condition that may prompt a wake event includes, determining by the control circuit that the user's heart rate is outside of a heart rate range. For example, the user's heart rate may differ from a target heart rate by more than a threshold amount and/or may exceed a high-end heartrate threshold or be lower than a low-end heart rate threshold. Another example of a user sleep condition that may prompt a wake event includes determining by the control circuit that the user's breathing rate is outside of a breathing rate range. For example, the user's breathing rate may different from a target breathing rate by more than a threshold amount and/or may exceed a high-end breathing rate threshold or be lower than a low-end breathing rate threshold.

Other examples of user sleep conditions that may prompt a wake event include, determining by the control circuit that the user's head is in an undesirable sleep position, determining that the user's body is in an undesirable sleep position, determining that the user's temperature is too high or too low, etc. The control circuit may determine that the user's head and/or body are in an undesirable position in any suitable manner. In some examples, one or more motion sensors may be calibrated to positions of the users head or body. For example, the sleep management device and/or companion device may prompt the user to assume requested positions of the user's head or body. The control circuit may receive signals from one or more motion sensors with the user's head and/or body at the requested positions. From the received signals, the control circuit may generate calibration data mapping motion sensor signals to locations of the user's head and/or body. When the control circuit receives a motion sensor signal or set of motion sensor signals that indicate, according to the calibration, that the user's head and/or body is in an undesirable position, it may detect a wake event. Also, in some examples, the control circuit may store a set of reference motion sensor signal signatures that correspond to undesirable body or head positions. If the control circuit detects actuation motion sensor signals corresponding to such motion sensor signal signature, a wake event may be detected. Other examples of wake events detected due to user sleep conditions are described herein with respect to FIG. 13.

At action 424, the sleep management device may select a wake routine associated with the detected wake event. In some examples, different wake events may be associated with different wake routines. For example, a scheduled wake event (e.g., based on a scheduled appointment of the user or other scheduled event) may be detected with enough lead time to implement a wake routine with a standard duration. Unscheduled wake events, for example, due to newly scheduled events, may prompt the sleep management device to select an expedited wake routine. An expedited wake routine may have a duration shorter than a standard wake routine, yet not immediate. Emergency wake events (e.g., an alarm in the vicinity, an approaching person, etc.) may prompt the sleep management device to select immediate wake routines. An immediate wake routine, for example, may provide bright and/or blinking visible output and loud sound output, for example, similar to an alarm clock. In this way, an immediate wake routine may awaken the user as soon as possible. Accordingly, the duration of an immediate wake routine may be shorter than that of an expedited wake routine. At action 426, the sleep management device may generate visible and/or sound sensory output according to the selected wake routine.

In some examples, the control circuit may also select a start time for the wake routine. For example, the start time for a wake routine may be selected to occur a threshold time before the user's next scheduled appointment. The threshold time may be any suitable time and may allow the user to wake up and prepare for the appointment.

As indicated by action 422, in some examples, the sleep management device may be programmed to periodically determine whether it has detected a wake event while the user is sleeping. The sleep management device may determine that the user is sleeping, for example, if the sleep management device has executed a sleep inducement routine without yet executing a corresponding wake routine. In some examples, the sleep management device may determine that the user is sleeping, for example, based on user conditions detected by the sensor or sensors of the sleep management device. In some examples, if the user falls asleep after a wake up event and wake routine (with or without an intervening sleep inducement routine) the sleep management device may continue to execute the process flow 420. In one example use case, the sleep management device may detect a wake event resulting in an expedited or immediate wake routine. Afterwards, the user may fall asleep again. Another wake event may occur at a scheduled wake-up time, which may result in a standard duration wake routine (e.g., longer than the duration of the expedited or immediate wake routine).

Figure 11:
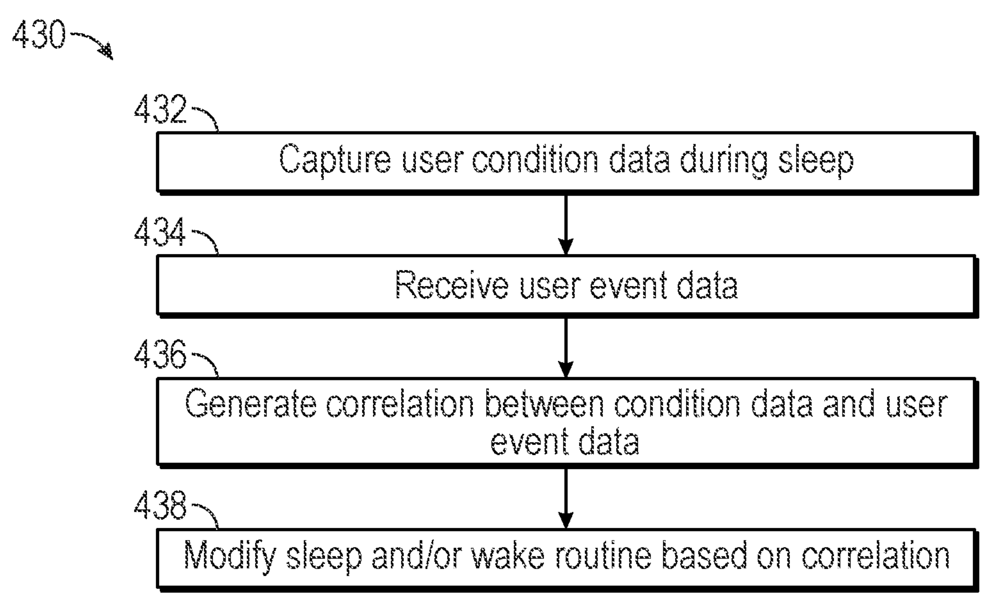
FIG. 11 is a flow chart showing one example of a process flow that may be executed by the sleep management device to refine sleep and/or wake routines.

FIG. 11 is a flow chart showing one example of a process flow 430 that may be executed by the sleep management device to refine sleep and/or wake routines. At action 432, the sleep management device may capture one or more user conditions while the user sleeps. Example user conditions may include user temperature, heart rate, breathing rate, body position, head position, etc. In some examples, user conditions may include the stage of the user's sleep, for example, based at least in part on eye movements of the user detected via the motion sensors 222. Example stages of the user's sleep may include Stage 1, Stage 2, Stage 3, Stage 4, and Random Eye Movement (REM) sleep.

Optionally, at action 434, the sleep management device may receive user event data. User event data may describe user events occurring during sleep and/or before or after sleep. User event data may be captured by one or more user condition sensors of the sleep management device, received as calendar data, and/or captured by one or more ambient stimuli sensors of the sleep management device and/or a companion user device.

At action 436, the sleep management device may generate one or more correlations between condition data and user event data. A correlation may be generated when a particular user condition occurs at or near the same time as a user event. For example, the user's heart rate may drop one hour after the user has gone to sleep. Also, for example, the user may experience less REM sleep on nights before the user has an early morning appointment. At action 438, the sleep management device may modify one or more sleep and/or wake routines based on the correlations. For example, if the user's heart rate drops one hour after the user has gone to sleep, the sleep management device may lengthen the duration of a sleep inducement routine. Also, for example, if the user experiences less REM sleep on nights before an early appointment, the sleep management device may modify a sleep or wake routine in a manner that increases REM sleep. Also, in some examples, the sleep management device may provide sound and/or visual output to the user during sleep to increase REM sleep. In some examples, user event data may include feedback data received from the user. For example, the user may be prompted by the device and/or a companion computing device to provide feedback about how well they slept.

Figure 12:
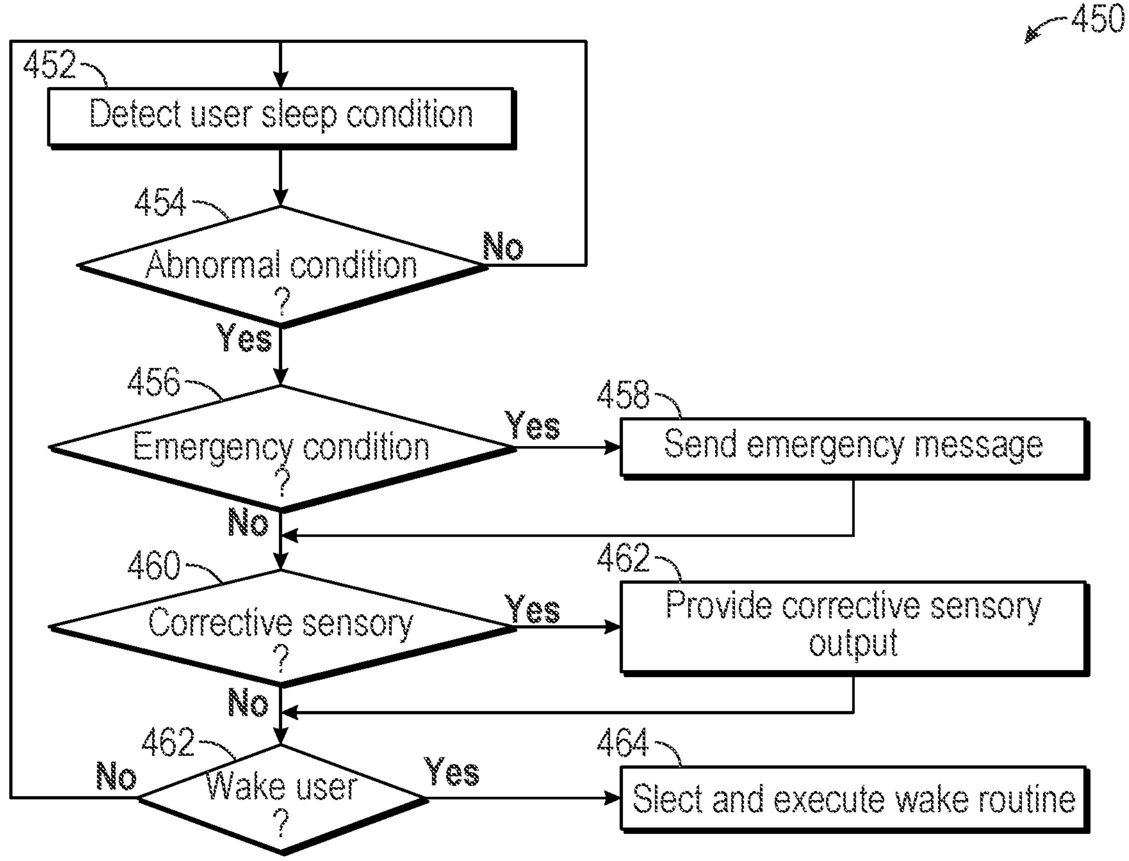
FIG. 12 is a flow chart showing one example of a process flow that may be executed by the sleep management device to modify a user's sleep in response to user sleep conditions.

FIG. 12 is a flow chart showing one example of a process flow 450 that may be executed by the sleep management device to modify a user's sleep in response to user sleep conditions. At action 452, the sleep management device may capture user condition data during user sleep. The user condition data may include, for example, a skin temperature of the user, a heart rate of the user, a breathing rate of the user, a head orientation of the user, a body orientation of the user, a sleep stage of the user, etc. User condition data may be captured, for example, as described herein.

At action 454, the sleep management device may determine whether the user conditions captured at 452 are abnormal. Conditions may be abnormal, for example, if the conditions are outside of an expected range of user conditions at the current stage of sleep, either in general or specifically for the user. If no abnormal condition is detected, in some examples, the sleep management device ma continue to periodically capture condition data at action 452.

If an abnormal user condition is detected at action 454, the sleep management device may, at 456, determine whether the abnormal condition is an emergency condition. An emergency condition may be a condition that might call for emergency assistance. An example emergency condition may occur if the user's temperature rises above a fever threshold, if the user's heart rate drops below a heart rate threshold, if the user's breathing rate drops below a breathing rate threshold, etc. The control circuit may detect an emergency condition, for example, by comparing the detected condition to a list of condition types that are emergency conditions. If the detected condition matches an emergency condition type included in the list, the control circuit may consider the detected condition to be an emergency condition.

If an emergency condition is detected at action 456, the sleep management device may send an emergency message at 458. The emergency message, in some examples, includes data describing the emergency condition. In examples where the emergency condition is a wake event, then, the emergency message may include data describing the wake event. The emergency message may be sent in any suitable manner and to any suitable recipient. In some examples, the emergency message may be sent to a police, fire department, paramedic or other suitable emergency personnel. In some examples where the user is on an aircraft, the emergency message may be sent to a flight attendant. The sleep management device may send the emergency message directly or indirectly via the companion device. For example, the sleep management device may send an emergency message request to the companion computing device. The device interface application 126 may receive the emergency message request and may send the emergency message, for example, via a packet-switched network and/or a mobile telephone network.

At action 460, the sleep management device may determine if corrective sensory output can or will be used in response to the detected user condition. Corrective sensory output may be used, for example, to modify the user condition. The sleep management device may store data indicating whether corrective sensory output is available and/or appropriate for the user condition captured at 452. If corrective sensory output is to be provided, the sleep management device may do so at action 462. Additional examples for providing corrective sensory output are provided herein, for example, at FIG. 13.

At 462, the sleep management device may determine whether to wake the user in response to the condition captured at 452. The sleep management device may wake the user, for example, to allow the user to address the sleep condition. For example, if the sleep condition is that the user is sleeping in a dangerous or uncomfortable sleeping condition, the sleep management device may determine to wake the user to allow the user to assume a different position. In some examples, the sleep management device may determine to wake a user when corrective sensory output is attempted, for example, if the corrective sensory output is unsuccessful in mitigating the user condition. If the sleep management device determines to wake the user, it may represent a wake event, as described above. The sleep management device may select and execute a wake routine at action 464, for example, as described herein with FIG. 10. In some examples, the sleep management device may select wake routine based at least in part on the detected sleep condition. For example, if the sleep condition is a body or head orientation that might cause pain or harm, the sleep management device may select an immediate wake routine. If the sleep condition is not as urgent, the sleep management device may select an intermediate and/or standard wake routine. If the sleep management device determines at action 462 not to wake the user it may, in some examples, return to action 452 and continue to monitor and/or capture user sleep conditions.

Figure 13:
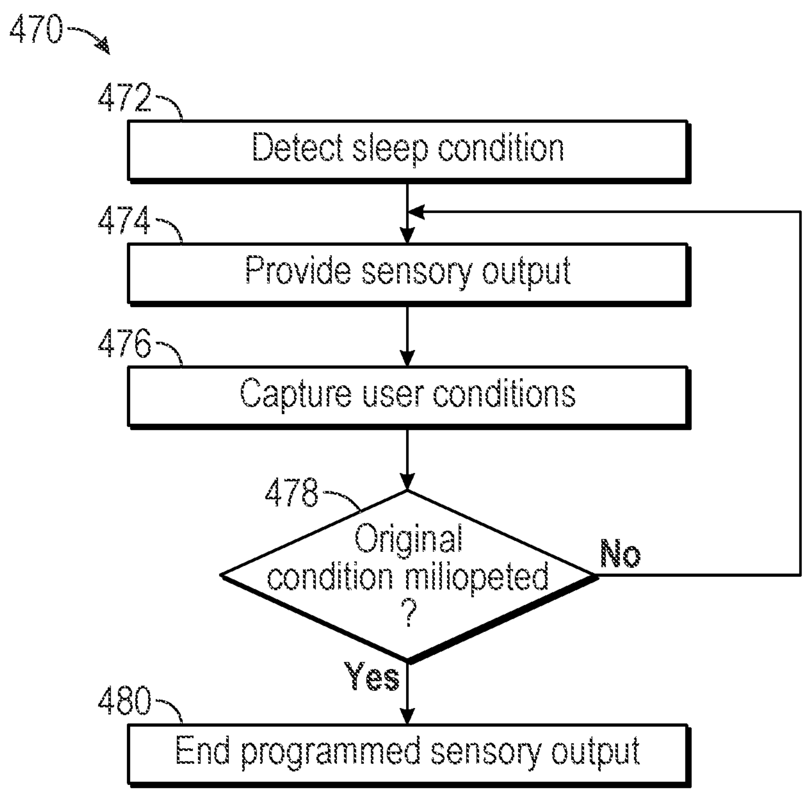
FIG. 13 is a flow chart showing one example of a process flow that may be executed by the sleep management device to provide corrective sensory output to modify a user sleep condition.

FIG. 13 is a flow chart showing one example of a process flow 470 that may be executed by the sleep management device to provide corrective sensory output to modify a user sleep condition. At action 472, the sleep management device may detect a user sleep condition, for example, as described herein above with respect to action 452. At action 474, the sleep management device may provide sensory output. The sensory output may be sound and/or visible output according to any suitable pattern. At action 476, the sleep management device capture additional user conditions to determine if the condition detected at action 472 has mitigated. The control circuit may determine if a user condition has mitigated by receiving additional sensor signals and re-measuring the condition. A condition may be mitigated if it has changed by more than a threshold amount. For example, if the user condition is a user head position, the head position may be mitigated when the user has moved his or her head by more than a threshold amount. Also, in some examples, a condition may be mitigated if it moves within mitigation thresholds. For example, if the user condition is that the user's breathing rate is too high, the condition may be mitigated if the user's breathing rate falls below a mitigation threshold. The mitigation threshold may be the same threshold used to detect the user condition, or a different threshold. If the condition has not mitigated, then the sleep management device may continue to provide sensory output at action 474 and proceed again from action 474 to actions 476 and 478. If the condition detected at 472 has mitigated, then the sleep management device may end the programmed sensory output at action 480.

Various examples described herein may be implemented in one or a combination of hardware, firmware, and software. Some examples may also be implemented as instructions stored on a machine-readable storage device, which may be read and executed by at least one processor to perform the operations described herein. A machine-readable storage device may include any non-transitory mechanism for storing information in a form readable by a machine (e.g., a computer). For example, a machine-readable storage device may include read-only memory (ROM), random-access memory (RAM), magnetic disk storage media, optical storage media, flash-memory devices, and other storage devices and media.

A processor subsystem may be used to execute the instruction on the machine-readable medium. The processor subsystem may include one or more processors, each with one or more cores. Additionally, the processor subsystem may be disposed on one or more physical devices. The processor subsystem may include one or more specialized processors, such as a graphics processing unit (GPU), a digital signal processor (DSP), a field programmable gate array (FPGA), or a fixed function processor.

Various examples, as described herein, may include, or may operate on, logic or a number of components, modules, or mechanisms. Modules may be hardware, software, or firmware communicatively coupled to one or more processors in order to carry out the operations described herein. Modules may be hardware modules, and as such modules may be considered tangible entities capable of performing specified operations and may be configured or arranged in a certain manner. In an example, circuits may be arranged (e.g., internally or with respect to external entities such as other circuits) in a specified manner as a module. In an example, the whole or part of one or more computer systems (e.g., a standalone, client or server computer system) or one or more hardware processors may be configured by firmware or software (e.g., instructions, an application portion, or an application) as a module that operates to perform specified operations. In an example, the software may reside on a machine-readable medium. In an example, the software, when executed by the underlying hardware of the module, causes the hardware to perform the specified operations. Accordingly, the term hardware module is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, each of the modules need not be instantiated at any one moment in time. For example, where the modules comprise a general-purpose hardware processor configured using software; the general-purpose hardware processor may be configured as respective different modules at different times. Software may accordingly configure a hardware processor, for example, to constitute a particular module at one instance of time and to constitute a different module at a different instance of time. Modules may also be software or firmware modules, which operate to perform the methodologies described herein.

Figure 14:
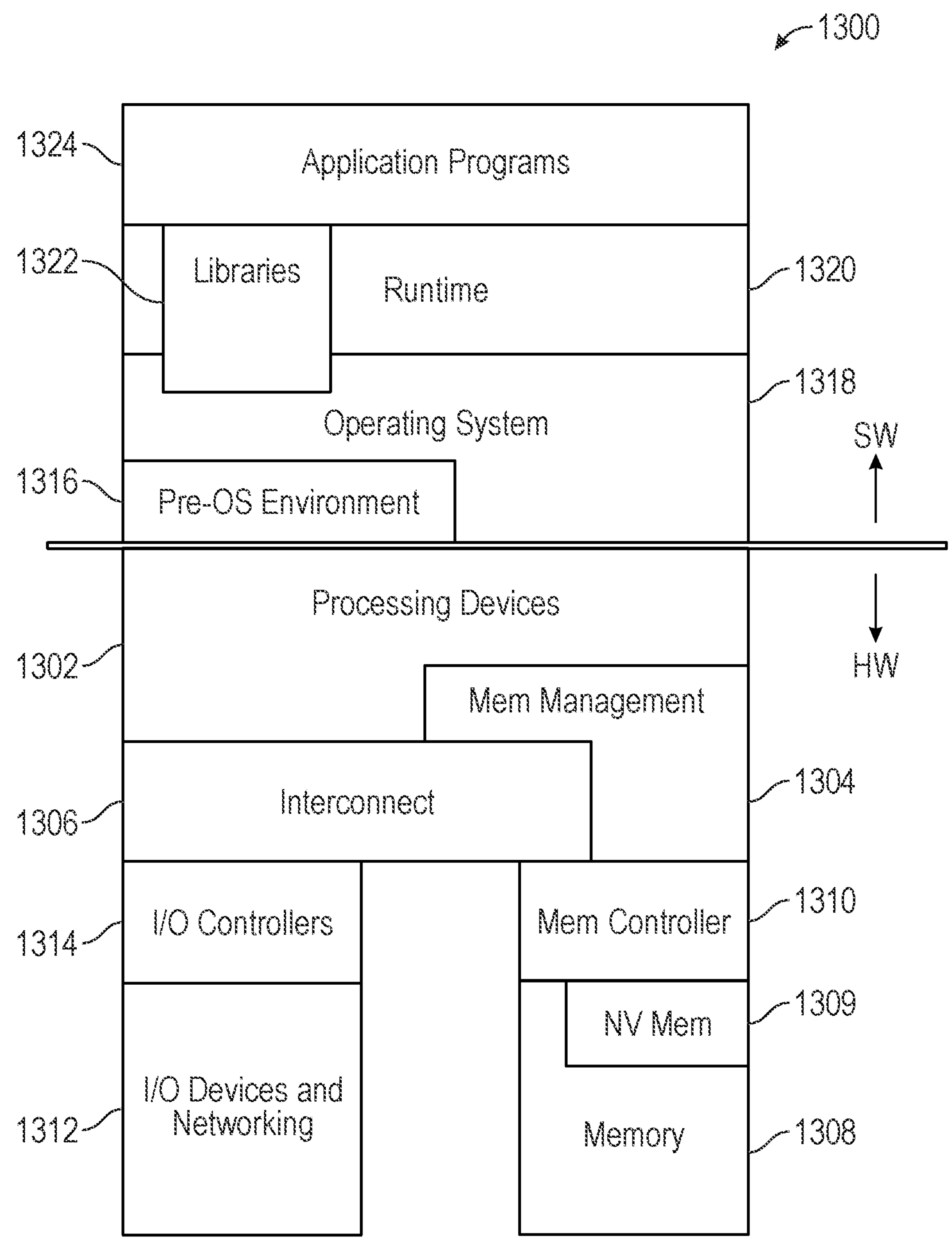
FIG. 14 is a diagram showing one example of a hardware and software architecture for a computing device.

FIG. 14 is a diagram showing one example of a hardware and software architecture 1300 for a computing device. The architecture 1300, for example, may be implemented in various systems described herein including, for example, the sleep management device, the companion device, the external system, etc. As indicated by HW, hardware components are represented below the divider line, whereas software components denoted by SW reside above the divider line. On the hardware side, processing devices 1302 (which may include one or more microprocessors, digital signal processors, etc., each having one or more processor cores, are interfaced with memory management device 1304 and system interconnect 1306. Memory management device 1304 provides mappings between virtual memory used by processes being executed, and the physical memory. Memory management device 1304 may be an integral part of a central processing unit which also includes the processing devices 1302.

Interconnect 1306 includes a backplane such as memory, data, and control lines, as well as the interface with input/output devices, e.g., PCI, USB, etc. Memory 1308 (e.g., dynamic random access memory—DRAM) and non-volatile memory 1309 such as flash memory (e.g., electrically-erasable read-only memory—EEPROM, NAND Flash, NOR Flash, etc.) are interfaced with memory management device 1304 and interconnect 1306 via memory controller 1310. This architecture may support direct memory access (DMA) by peripherals in one type of example. I/O devices, including video and audio adapters, non-volatile storage, external peripheral links such as USB, Bluetooth, etc., as well as network interface devices such as those communicating via Wi-Fi or LTE-family interfaces, are collectively represented as I/O devices and networking 1312, which interface with interconnect 1306 via corresponding I/O controllers 1314. For example, I/O controllers 1314 may be configured to drive components of the sleep management device such as, LEDs or other illumination sources, various communications links, etc. Also, in some examples, I/O controllers 1314 may facilitate communications with external systems, such as 110.

On the software side, a pre-operating system (pre-OS) environment 1316, which is executed at initial system start-up and is responsible for initiating the boot-up of the operating system. One example of pre-OS environment 1316 is a system basic input/output system (BIOS). In present-day systems, a unified extensible firmware interface (UEFI) is implemented. Pre-OS environment 1316, is responsible for initiating the launching of the operating system, but also provides an execution environment for embedded applications according to certain aspects of the invention.

Operating system (OS) 1318 provides a kernel that controls the hardware devices, manages memory access for programs in memory, coordinates tasks and facilitates multi-tasking, organizes data to be stored, assigns memory space and other resources, loads program binary code into memory, initiates execution of the application program which then interacts with the user and with hardware devices, and detects and responds to various defined interrupts. Also, operating system 1318 provides device drivers, and a variety of common services such as those that facilitate interfacing with peripherals and networking, that provide abstraction for application programs so that the applications do not need to be responsible for handling the details of such common operations. Operating system 1318 additionally provides a graphical user interface (GUI) module that facilitates interaction with the user via peripheral devices such as a monitor, keyboard, mouse, microphone sensor, video camera, touchscreen, and the like.

Runtime system 1320 implements portions of an execution model, including such operations as putting parameters onto the stack before a function call, the behavior of disk input/output (I/O), and parallel execution-related behaviors. Runtime system 1320 may also perform support services such as type checking, debugging, or code generation and optimization.

Libraries 1322 include collections of program functions that provide further abstraction for application programs. These include shared libraries, dynamic linked libraries (DLLs), for example. Libraries 1322 may be integral to the operating system 1318, runtime system 1320, or may be added-on features, or even remotely-hosted. Libraries 1322 define an application program interface (API) through which a variety of function calls may be made by application programs 1324 to invoke the services provided by the operating system 1318. Application programs 1324 are those programs that perform useful tasks for users, beyond the tasks performed by lower-level system programs that coordinate the basis operability of the computing device itself.

Figure 15:
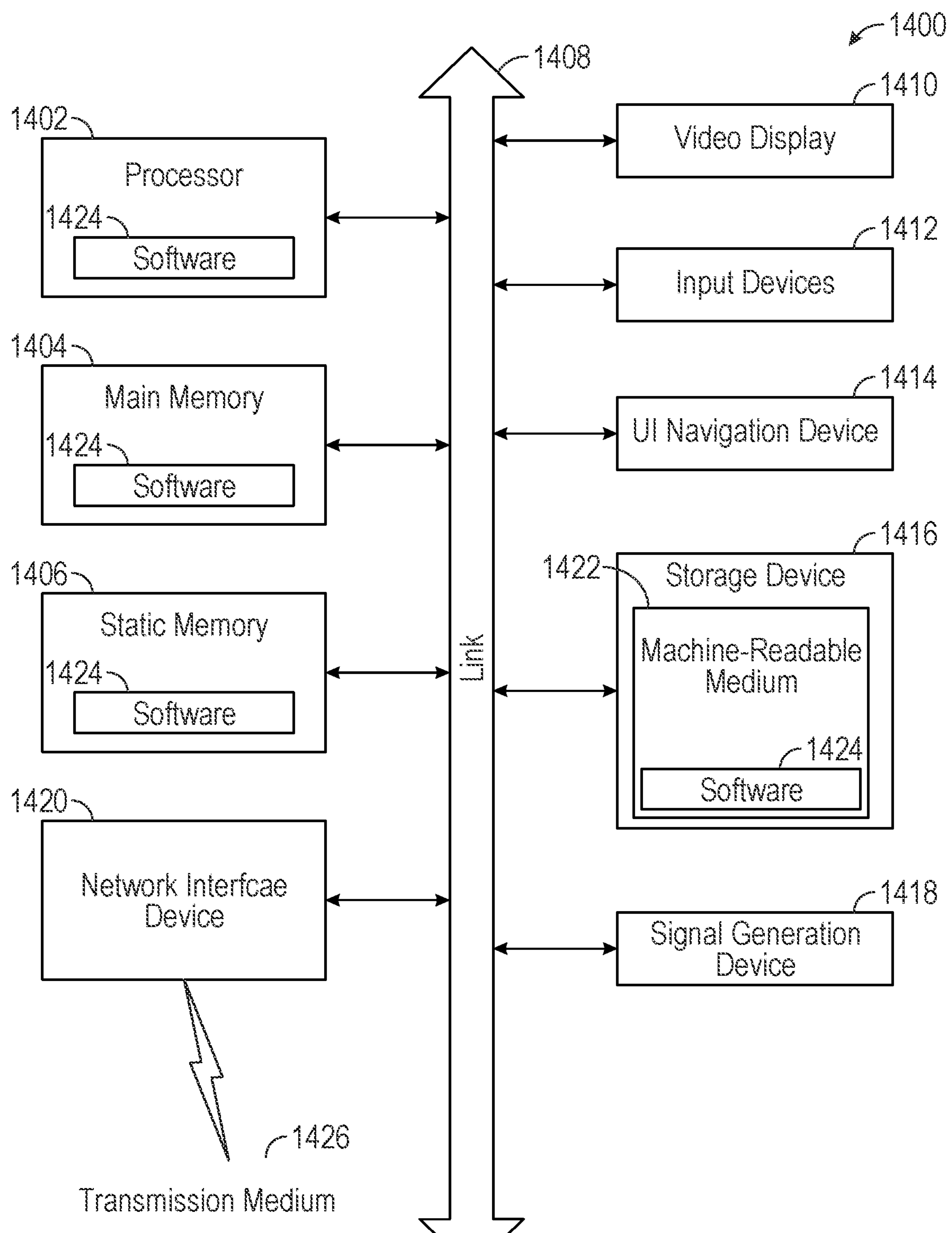
FIG. 15 is a block diagram showing one example of a computing device platform.

FIG. 15 is a block diagram showing one example of a computing device platform 1400. The platform 1400 may be implemented, for example in the sleep management device, in the companion computing device, in the external system, etc. In certain examples, programming of the computing device platform 1400 according to one or more particular algorithms produces a special-purpose machine upon execution of that programming. In a networked deployment, the computing device platform 1400 may operate in the capacity of either a server or a client machine in server-client network environments, or it may act as a peer machine in peer-to-peer (or distributed) network environments.

Example computing device platform 1400 includes at least one processor 1402 (e.g., a central processing unit (CPU), a graphics processing unit (GPU) or both, processor cores, compute nodes, etc.), a main memory 1404 and a static memory 1406, which communicate with each other via a link 1408 (e.g., bus). The computing device platform 1400 may further include a video display unit 1410, input devices 1412 (e.g., a keyboard, camera, microphone sensor), and a user interface (UI) navigation device 1414 (e.g., mouse, touchscreen). The computing device platform 1400 may additionally include a storage device 1416 (e.g., a drive unit), a signal generation device 1418 (e.g., a speaker), and a network interface device (NID) 1420.

The storage device 1416 includes a machine-readable medium 1422 on which is stored one or more sets of data structures and instructions 1424 (e.g., software) embodying or utilized by any one or more of the methodologies or functions described herein. The instructions 1424 may also reside, completely or at least partially, within the main memory 1404, static memory 1406, and/or within the processor 1402 during execution thereof by the computing device platform 1400, with the main memory 1404, static memory 1406, and the processor 1402 also constituting machine-readable media.

While the machine-readable medium 1422 is illustrated in an example to be a single medium, the term "machine-readable medium" may include a single medium or multiple media (e.g., a centralized or distributed database, and/or associated caches and servers) that store the one or more instructions 1424. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

NID 1420 according to various examples may take any suitable form factor. In one such example, NID 1420 is in the form of a network interface card (NIC) that interfaces with processor 1402 via link 1408. In one example, link 1408 includes a PCI Express (PCIe) bus, including a slot into which the NIC form-factor may removably engage. In another example, NID 1420 is a network interface circuit laid out on a motherboard together with local link circuitry, processor interface circuitry, other input/output circuitry, memory circuitry, storage device and peripheral controller circuitry, and the like. In another example, NID 1420 is a peripheral that interfaces with link 1408 via a peripheral input/output port such as a universal serial bus (USB) port. MD 1420 transmits and receives data over transmission medium 1426, which may be wired or wireless (e.g., radio frequency, infra-red or visible light spectra, etc.), fiber optics, or the like.

Examples, as described herein, may include, or may operate on, logic or a number of components, engines, or modules, circuits, which for the sake of consistency are termed circuits, although it will be understood that these terms may be used interchangeably. Circuits may be hardware, software, or firmware communicatively coupled to one or more processors in order to carry out the operations described herein. Circuits may be hardware circuits, and as such circuits may be considered tangible entities capable of performing specified operations and may be configured or arranged in a certain manner. In an example, circuits may be arranged (e.g., internally or with respect to external entities such as other circuits) in a specified manner as a circuit. In an example, the whole or part of one or more computing platforms (e.g., a standalone, client or server computing platform) or one or more hardware processors may be configured by firmware or software (e.g., instructions, an application portion, or an application) as a circuit that operates to perform specified operations. In an example, the software may reside on a machine-readable medium. In an example, the software, when executed by the underlying hardware of the circuit, causes the hardware to perform the specified operations. Accordingly, the term hardware circuit is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein.

Considering examples in which circuits are temporarily configured, each of the circuits need not be instantiated at any one moment in time. For example, where the circuits comprise a general-purpose hardware processor configured using software; the general-purpose hardware processor may be configured as respective different circuits at different times. Software may accordingly configure a hardware processor, for example, to constitute a particular circuit at one instance of time and to constitute a different circuit at a different instance of time.

ADDITIONAL NOTES & EXAMPLES

Example 1 is a sleep management device comprising: a display; an event circuit to detect a first wake event; a wake selection circuit communicatively coupled to the event circuit and to select a first wake routine associated with the first wake event; a wake execution circuit communicatively coupled to the wake selection circuit and to the event circuit, and to execute the first wake routine at least in part by modulating an output of the display for a first duration; wherein the event circuit is to detect a second wake event different than the first wake event; wherein the wake selection circuit is to select a second wake routine associated with the second wake event; and wherein the wake execution circuit is to execute the second wake routine at least in part by modulating the output of the display for a second duration longer than the first duration.

In Example 2, the subject matter of Example 1 optionally includes a microphone sensor positioned to detect ambient sound, wherein the event circuit is further programmed to receive from the microphone sensor a microphone sensor signal, wherein the detect of the first wake event is based at least in part on the microphone sensor signal.

In Example 3, the subject matter of Example 2 optionally includes wherein the event circuit is further programmed to determine that an intensity of the microphone sensor signal is greater than an intensity threshold.

In Example 4, the subject matter of any one or more of Examples 2-3 optionally includes, wherein the event circuit is further programmed to: compare the microphone sensor signal to an ambient reference sound signal; and determine that the microphone sensor signal differs from the ambient reference sound signal by less than a difference threshold.

In Example 5, the subject matter of any one or more of Examples 1-4 optionally includes, further comprising a microphone sensor positioned to receive sound originating from a user of the sleep management device, wherein the event circuit is further programmed to receive from the microphone sensor a microphone sensor signal, and wherein the detect of the first wake event is based at least in part on the microphone sensor signal.

In Example 6, the subject matter of Example 5 optionally includes wherein the event circuit is further programmed to: detect from the microphone sensor signal a heartbeat signal indicating a heartbeat of the user; determine a heart rate of the user from the heartbeat signal; and determine that the heart rate of the user differs from a target heart rate by more than a heart rate threshold.

In Example 7, the subject matter of any one or more of Examples 5-6 optionally includes, wherein the event circuit is further programmed to: detect from the microphone sensor signal a breathing signal indicating breathing of the user; determine a breathing rate of the user from the breathing signal; and determine that the breathing rate of the user differs from a target breathing rate by more than a breathing rate threshold.

In Example 8, the subject matter of any one or more of Examples 1-7 optionally includes, wherein the wake execution circuit is further programmed to send an emergency message to a second computing device based at least in part on the detect of the first wake event, wherein the emergency message comprises data describing the first wake event.

In Example 9, the subject matter of any one or more of Examples 1-8 optionally includes, further comprising a motion sensor positioned to sense motion of a user of the sleep management device, wherein the event circuit is further programmed to receive from the motion sensor a motion signal, and wherein the detect of the first wake event is based at least in part on the motion signal.

In Example 10, the subject matter of Example 9 optionally includes wherein the event circuit is further programmed to: compare the motion signal to a first reference motion signal describing an undesirable body position of the user; and determine that the motion signal differs from the first reference motion signal by less than a motion threshold.

In Example 11, the subject matter of any one or more of Examples 1-10 optionally includes, wherein the event circuit is further programmed to: receive from a second computing device a message indicating an appointment scheduled at a first time; determine a second wake routine start time based at least in part on the first time; and begin the execute of the second wake routine at the second wake routine start time.

In Example 12, the subject matter of any one or more of Examples 1-11 optionally includes, wherein to detect the second wake event, the event circuit, at least: retrieves a calendar data from a memory of the sleep management device; and determines that the calendar data describes an appointment of a user of the sleep management device within a threshold time of the determining.

In Example 13, the subject matter of any one or more of Examples 1-12 optionally includes, further comprising a speaker, wherein to execute the first wake routine, the event circuit, at least, modulates an output of the speaker.

In Example 14, the subject matter of any one or more of Examples 1-13 optionally includes, wherein the display comprises: a multi-color illumination source; an optical splitter comprising an optical input optically coupled to the illumination source, a first optical output optically coupled to the illumination source and a second optical output; a first light pipe having a first light pipe end optically coupled to the first optical output of the optical splitter and a second light pipe end; and a first passive light panel optically coupled to the second light pipe end.

In Example 15, the subject matter of any one or more of Examples 1-14 optionally includes, further comprising: a front frame portion having a proximal side directed towards a user wearing the sleep management device and a distal side directed away from the user wearing the sleep management device; a first temple arm extending from the front frame portion; and a second temple arm extending from the front frame portion, wherein the display is positioned to illuminate from the proximal side of the front frame portion.

Example 16 is a method for operating a sleep management device, comprising: sleep management device comprising: detecting a first wake event; selecting a first wake routine associated with the first wake event; executing the first wake routine, wherein executing of the first wake routine comprises modulating an output of a display of the sleep management device for a first duration; detecting a second wake event different than the first wake event; selecting a second wake routine associated with the second wake event; and executing the second wake routine, wherein executing the second wake routine comprises modulating the output of the display for a second duration longer than the first duration.

In Example 17, the subject matter of Example 16 optionally includes wherein detecting the first wake event comprises determining that an intensity of a microphone sensor signal is greater than an intensity threshold.

In Example 18, the subject matter of any one or more of Examples 16-17 optionally includes wherein detecting the first wake event comprises: comparing a microphone sensor signal to an ambient reference sound signal; and determining that the microphone sensor signal differs from the ambient reference sound signal by less than a difference threshold.

In Example 19, the subject matter of any one or more of Examples 16-18 optionally includes, further comprising receiving a microphone sensor signal from a microphone sensor positioned to receive sound originating from a user of the sleep management device, wherein the detecting of the first wake event is based at least in part on the microphone sensor signal.

In Example 20, the subject matter of Example 19 optionally includes detecting from the microphone sensor signal a heartbeat signal indicating a heartbeat of the user; determining a heart rate of the user from the heartbeat signal; and determining that the heart rate of the user differs from a target heart rate by more than a heart rate threshold.

In Example 21, the subject matter of any one or more of Examples 19-20 optionally includes, further comprising: detecting from the microphone sensor signal a breathing signal indicating breathing of the user; determining a breathing rate of the user from the breathing signal; and determining that the breathing rate of the user differs from a target breathing rate by more than a breathing rate threshold.

In Example 22, the subject matter of any one or more of Examples 16-21 optionally includes, further comprising sending an emergency message to a second computing device based at least in part on the detect of the first wake event, wherein the emergency message comprises data describing the first wake event.

In Example 23, the subject matter of any one or more of Examples 16-22 optionally includes, further comprising receiving from a motion sensor a motion signal, wherein the motion sensor is positioned to sense motion of a user of the sleep management device, and wherein the detecting of the first wake event is based at least in part on the motion signal.

In Example 24, the subject matter of Example 23 optionally includes comparing the motion signal to a first reference motion signal describing an undesirable body position of the user; and determining that the motion signal differs from the first reference motion signal by less than a motion threshold In Example 25, the subject matter of any one or more of Examples 16-24 optionally includes, further comprising: receiving from a second computing device a message indicating an appointment scheduled at a first time; determining a second wake routine start time based at least in part on the first time; and beginning the execute of the second wake routine at the second wake routine start time In Example 26, the subject matter of any one or more of Examples 16-25 optionally includes, further comprising: retrieving a calendar data from a memory of the sleep management device; and determining that the calendar data describes an appointment of a user of the sleep management device within a threshold time of the determining.

In Example 27, the subject matter of any one or more of Examples 16-26 optionally includes, further comprising modulating an output of a speaker of the sleep management device.

Example 28 is at least one computer-readable medium comprising instructions to perform one of the methods of Examples 16-27.

Example 29 is an apparatus comprising means for performing one of the methods of Examples 16-27.

Example 30 is an apparatus comprising: means for detecting a first wake event; means for selecting a first wake routine associated with the first wake event; means for executing the first wake routine, wherein executing of the first wake routine comprises modulating an output of a display of the sleep management device for a first duration; means for detecting a second wake event different than the first wake event; means for selecting a second wake routine associated with the second wake event; and means for executing the second wake routine, wherein executing the second wake routine comprises modulating the output of the display for a second duration longer than the first duration.

In Example 31, the subject matter of Example 30 optionally includes wherein detecting the first wake event comprises determining that an intensity of a microphone sensor signal is greater than an intensity threshold.

In Example 32, the subject matter of any one or more of Examples 30-31 optionally includes wherein detecting the first wake event comprises: comparing a microphone sensor signal to an ambient reference sound signal; and determining that the microphone sensor signal differs from the ambient reference sound signal by less than a difference threshold.

In Example 33, the subject matter of any one or more of Examples 30-32 optionally includes, further comprising means for receiving a microphone sensor signal from a microphone sensor positioned to receive sound originating from a user of the sleep management device, wherein the detecting of the first wake event is based at least in part on the microphone sensor signal.

In Example 34, the subject matter of Example 33 optionally includes means for: means for detecting from the microphone sensor signal a heartbeat signal indicating a heartbeat of the user; means for determining a heart rate of the user from the heartbeat signal; and means for determining that the heart rate of the user differs from a target heart rate by more than a heart rate threshold.

In Example 35, the subject matter of any one or more of Examples 33-34 optionally includes, further comprising: means for detecting from the microphone sensor signal a breathing signal indicating breathing of the user; means for determining a breathing rate of the user from the breathing signal; and means for determining that the breathing rate of the user differs from a target breathing rate by more than a breathing rate threshold.

In Example 36, the subject matter of any one or more of Examples 30-35 optionally includes, further comprising means for sending an emergency message to a second computing device based at least in part on the detect of the first wake event, wherein the emergency message comprises data describing the first wake event.

In Example 37, the subject matter of any one or more of Examples 30-36 optionally includes, further comprising means for receiving from a motion sensor a motion signal, wherein the motion sensor is positioned to sense motion of a user of the sleep management device, and wherein the detecting of the first wake event is based at least in part on the motion signal.

In Example 38, the subject matter of Example 37 optionally includes means for comparing the motion signal to a first reference motion signal describing an undesirable body position of the user; and means for determining that the motion signal differs from the first reference motion signal by less than a motion threshold.

In Example 39, the subject matter of any one or more of Examples 30-38 optionally includes, further comprising: means for receiving from a second computing device a message indicating an appointment scheduled at a first time; means for determining a second wake routine start time based at least in part on the first time; and means for beginning the execute of the second wake routine at the second wake routine start time.

In Example 40, the subject matter of any one or more of Examples 30-39 optionally includes, further comprising: means for retrieving a calendar data from a memory of the sleep management device; and means for determining that the calendar data describes an appointment of a user of the sleep management device within a threshold time of the determining.

Example 41 is a sleep management device comprising: a display; a sensor positioned to sense a condition of a user of the sleep management device; an event circuit to: receive a first sensor signal from the sensor; and determine that the first sensor signal indicates a first condition of the first user; a sleep execution circuit to modulate the display according to a first sleep modification routine; wherein the event circuit is to receive a second sensor signal from the sensor; and determine that the second sensor signal indicates that the first condition of the user is mitigated.

In Example 42, the subject matter of Example 41 optionally includes wherein the event circuit is to determine that the first condition is outside of an expected range.

In Example 43, the subject matter of any one or more of Examples 41-42 optionally includes, wherein the event circuit is to: determine that the first condition is an emergency condition; and send an emergency message comprising data describing the first condition.

In Example 44, the subject matter of one or more of Examples 41-43 optionally includes, wherein the event circuit is to determine that the second sensor signal is within a mitigation range.

In Example 44, the subject matter of any one or more of Examples 41-43 optionally includes, wherein the sensor comprises a motion sensor and the first condition is comprises a position of a head of the user.

In Example 45, the subject matter of any one or more of Examples 41-44 optionally includes, wherein the sensor comprises microphone sensor and the first condition is comprises a breathing rate of the user.

In Example 46, the subject matter of any one or more of Examples 41-45 optionally includes, wherein the sensor comprises a microphone sensor and the first condition comprises a heart rate of the user.

Example 47 is a method, comprising: receiving a first sensor signal from a sensor positioned to sense a condition of a user of a sleep management device; determining that the first sensor signal indicates a first condition of the user; modulating a display according to a first sleep modification routine; receiving a second sensor signal from the sensor; and determining that the second sensor signal indicates that the first condition of the user is mitigated.

In Example 48, the subject matter of Example 47 optionally includes determining that the first condition is outside of an expected range.

In Example 49, the subject matter of any one or more of Examples 47-48 optionally includes, further comprising: determining that the first condition is an emergency condition; and sending an emergency message comprising data describing the first condition.

In Example 50, the subject matter of any one or more of Examples 47-49 optionally includes, further comprising determining that the second sensor signal is within a mitigation range.

In Example 51, the subject matter of any one or more of Examples 47-50 optionally includes, wherein the sensor comprises a motion sensor and the first condition comprises a position of a head of the user.

In Example 52, the subject matter of any one or more of Examples 47-51 optionally includes, wherein the sensor comprises microphone sensor and the first condition comprises a breathing rate of the user.

In Example 53, the subject matter of any one or more of Examples 47-52 optionally includes, wherein the sensor comprises a microphone sensor and the first condition comprises a heart rate of the user.

Example 54 is at least one computer-readable medium comprising instructions to perform one of the methods of Examples 47-53.

Example 55 is an apparatus comprising means for performing one of the methods of Examples 47-53.

Example 56 is an apparatus comprising: means for receiving a first sensor signal from a sensor positioned to sense a condition of a user of a sleep management device; means for determining that the first sensor signal indicates a first condition of the user; means for modulating a display according to a first sleep modification routine; means for receiving a second sensor signal from the sensor; and means for determining that the second sensor signal indicates that the first condition of the user is mitigated.

In Example 57, the subject matter of Example 56 optionally includes means for determining that the first condition is outside of an expected range.

In Example 58, the subject matter of any one or more of Examples 56-57 optionally includes, further comprising: means for determining that the first condition is an emergency condition; and means for sending an emergency message comprising data describing the first condition.

In Example 59, the subject matter of any one or more of Examples 56-58 optionally includes, further comprising means for determining that the second sensor signal is within a mitigation range.

In Example 60, the subject matter of any one or more of Examples 56-59 optionally includes, wherein the sensor comprises a motion sensor and the first condition comprises a position of a head of the user.

In Example 61, the subject matter of any one or more of Examples 56-60 optionally includes, wherein the sensor comprises microphone sensor and the first condition comprises a breathing rate of the user.

In Example 62, the subject matter of any one or more of Examples 56-61 optionally includes, wherein the sensor comprises a microphone sensor and the first condition comprises a heart rate of the user.

The above detailed description includes references to the accompanying drawings, which form a part of the detailed description. The drawings show, by way of illustration, specific examples that may be practiced. These examples are also referred to herein as "examples." Such examples may include elements in addition to those shown or described. However, also contemplated are examples that include the elements shown or described. Moreover, also contemplated are examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to suggest a numerical order for their objects.

The above description is intended to be illustrative, and not restrictive. For example, the above-described examples (or one or more aspects thereof) may be used in combination with others. Other examples may be used, such as by one of ordinary skill in the art upon reviewing the above description. The Abstract is to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. However, the claims may not set forth every feature disclosed herein as examples may feature a subset of said features. Further, examples may include fewer features than those disclosed in a particular example. Thus, the following claims are hereby incorporated into the Detailed Description, with a claim standing on its own as a separate example. The scope of the examples disclosed herein is to be determined with reference to the appended claims, along with the full scope of equivalents to which such claims are entitled.

What is claimed is:

1. A sleep management device comprising:
- a front frame portion having a proximal side positioned to be directed towards a user when the sleep management device is worn by the user and a distal side directed away from the user when the sleep management device is worn by the user;
- a display positioned to illuminate from the proximal side of the front frame portion;
- a motion sensor positioned to sense motion of the user of the sleep management device;
- an event circuit to:
  - determine a sleep time for the user of the sleep management device based at least in part on future time zone data describing a time zone that the user is to be in at a future time, wherein the event circuit is to generate a sleep instruction based at least in part on the sleep time;
  - receive a motion signal from the motion sensor;
  - compare the motion signal to a first reference motion signal describing a first body position of the user; and
  - detect a first wake event at least in part by determining that the motion signal differs from the first reference motion signal by less than a motion threshold;
- a sleep routine execution circuit communicatively coupled to the event circuit and to receive the sleep instruction, wherein the sleep routine execution circuit is to execute a sleep inducement routine responsive to the sleep instruction; and
- a wake execution circuit communicatively coupled to the event circuit, and to execute a first wake routine by modulating an output of the display.

2. The sleep management device of claim 1, wherein the display comprises a multi-color illumination source.

3. The sleep management device of claim 2, wherein the display comprises:
- an optical splitter comprising an optical input optically coupled to the multi-color illumination source, a first optical output optically coupled to the multi-color illumination source and a second optical output;
- a first light pipe having a first light pipe end optically coupled to the first optical output of the optical splitter and a second light pipe end; and
- a first passive light panel optically coupled to the second light pipe end.

4. The sleep management device of claim 1, wherein the event circuit is to:
- receive from a computing device a message indicating an appointment scheduled at a first time;
- determine a first wake routine start time based at least in part on the first time; and
- begin the execution of the first wake routine at the first wake routine start time.

5. The sleep management device of claim 1, further comprising a memory, wherein the event circuit is to detect the first wake event by:
- retrieving calendar data from the memory of the sleep management device; and
- determining that the calendar data describes an appointment of the user within a threshold time.

6. The sleep management device of claim 1, further comprising a microphone sensor positioned to detect ambient sound, wherein the event circuit is to receive from the microphone sensor a microphone sensor signal, wherein the event circuit is to detect the first wake event based at least in part on the microphone sensor signal.

7. The sleep management device of claim 1, further comprising a microphone sensor positioned to receive sound originating from the user of the sleep management device, wherein the event circuit is to receive from the microphone sensor a microphone sensor signal, and wherein the event circuit is to detect the first wake event based at least in part on the microphone sensor signal.

8. The sleep management device of claim 7, wherein the event circuit is to:
- detect from the microphone sensor signal at least one of a heartbeat signal indicating a heartbeat of the user or a breathing signal indicating breathing of the user; and
- using the microphone sensor signal, determine that a physiological condition of the user is outside of a threshold range.

9. The sleep management device of claim 1, wherein the event circuit is to detect the first wake event, and wherein the execution of the first wake routine is responsive to the detection of the first wake event, further comprising a wake selection circuit:
- wherein the event circuit is to detect a second wake event different than the first wake event;
- wherein the wake selection circuit is to select a second wake routine associated with the second wake event; and wherein the wake execution circuit is to execute the first wake routine by modulating the output of the display for a first duration and is to execute the second wake routine by modulating the output of the display for a second duration longer than the first duration.

10. The sleep management device of claim 1, further comprising a speaker, wherein to execute the sleep inducement routine, the event circuit modulates an output of the speaker.

11. The sleep management device of claim 1, further comprising a wake selection circuit communicatively coupled to the event circuit and to select the first wake routine based at least in part on the first wake event detected by the event circuit.

12. The sleep management device of claim 1, further comprising:

a first temple arm extending from the front frame portion; and a second temple arm extending from the front frame portion.

13. A method for operating a sleep management device comprising at least one processor; a front frame portion having a proximal side positioned to be directed towards a user when the sleep management device is worn by the user and a distal side directed away from the user when the sleep management device is worn by the user; and a display positioned to illuminate from the proximal side of the front frame portion, the method comprising:

determining, by the sleep management device, a sleep time for a user of the sleep management device, the determining based at least in part on future time zone data describing a time zone that the user is to be in at a future time;

based on the sleep time, determining, by the sleep management device, to execute a sleep inducement routine;

executing, by the sleep management device, the sleep inducement routine by modulating an output of the display;

receiving a motion signal from a motion sensor;

comparing the motion signal to a first reference motion signal describing a first body position of the user;

detecting a first wake event at least in part by determining that the motion signal differs from the first reference motion signal by less than a motion threshold; and executing, by the sleep management device, a first wake routine by modulating the output of the display.

14. The method of claim 13, comprising:

receiving, by the sleep management device and from a computing device, a message indicating an appointment scheduled at a first time;

determining, by the sleep management device, a first wake routine start time based at least in part on the first time; and beginning the executing of the first wake routine by the sleep management device at the first wake routine start time.

15. The method of claim 13, comprising detecting the first wake event, the detecting of the first wake event comprising: accessing calendar data from a memory of the sleep management device; and determining that the calendar data describes an appointment of the user within a threshold time.

16. The method of claim 13, wherein the executing of the sleep inducement routine comprises modulating an output of a speaker of the sleep management device.

17. At least one non-transitory computer readable medium comprising instructions thereon that, when executed by at least one processor, causes the at least one processor to perform operations comprising:

determining a sleep time for a user of a sleep management device, the determining based at least in part on future time zone data describing a time zone that the user is to be in at a future time, wherein the sleep management device comprises a front frame portion having a proximal side positioned to be directed towards a user when the sleep management device is worn by the user and a distal side directed away from the user when the sleep management device is worn by the user; and a display positioned to illuminate from the proximal side of the front frame portion;

based at least in part on the sleep time, determining to execute a sleep inducement routine;

executing the sleep inducement routine by modulating an output of the display;

receiving a motion signal from a motion sensor;

comparing the motion signal to a first reference motion signal describing a first body position of the user;

detecting a first wake event at least in part by determining that the motion signal differs from the first reference motion signal by less than a motion threshold; and executing a first wake routine by modulating the output of the display.

18. The at least one non-transitory computer readable medium of claim 17, the operations further comprising:

receiving from a computing device, a message indicating an appointment scheduled at a first time;

determining a first wake routine start time based at least in part on the first time; and beginning the executing of the first wake routine by the sleep management device at the first wake routine start time.

19. The at least one non-transitory computer readable medium of claim 17, the operations further comprising detecting the first wake event at least in part by:

accessing calendar data from a memory of the sleep management device; and determining that the calendar data describes an appointment of the user within a threshold time.

20. The at least one non-transitory computer readable medium of claim 17, wherein the executing of the sleep inducement routine comprises modulating an output of a speaker of the sleep management device.

* * * * *